(12) United States Patent
Cunnyngham et al.

(10) Patent No.: US 7,358,423 B1
(45) Date of Patent: Apr. 15, 2008

(54) INBRED MAIZE LINE PH87P

(75) Inventors: Charles T. Cunnyngham, Tipton, IN (US); Daniel P. Gorman, Tallahassee, FL (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 253 days.

(21) Appl. No.: 11/030,734

(22) Filed: Jan. 6, 2005

Related U.S. Application Data

(63) Continuation of application No. 10/355,633, filed on Jan. 31, 2003, now Pat. No. 6,888,051.

(51) Int. Cl.
*A01H 5/00* (2006.01)
*A01H 5/10* (2006.01)
*A01H 1/00* (2006.01)
*C12N 5/04* (2006.01)

(52) U.S. Cl. ................ 800/320.1; 800/275; 800/300.1; 800/302; 435/312

(58) Field of Classification Search ............. None
See application file for complete search history.

(56) References Cited

U.S. PATENT DOCUMENTS

| 5,436,390 | A | 7/1995 | Oestreich |
| 6,025,547 | A | 2/2000 | Stucker |
| 6,740,798 | B1 | 5/2004 | Hoffbeck |
| 6,881,880 | B1 | 4/2005 | Wilson et al. |

OTHER PUBLICATIONS

Goldman et al (1994) Crop Science 34(4): 908-915.*
U.S. Appl. No. 10/271,166, filed Oct. 15, 2002—Wilson et al., (Do Not Publish).
Plant Variety Protection Certificate No. 9800386 for Corn PHI1CA Jun. 14, 2001.
Plant Variety Protection Certificate No. 9700224 for Corn, Field PH32C Jan. 30, 2001.
Plant Variety Protection Certificate No. 9100097 for Corn, PHR03 Apr. 30, 1992.

* cited by examiner

*Primary Examiner*—Elizabeth F. McElwain
(74) *Attorney, Agent, or Firm*—McKee, Voorhees & Sease, P.L.C.

(57) ABSTRACT

An inbred maize line, designated PH87P, the seeds and plants of inbred maize line PH87P, methods for producing a maize plant, either inbred or hybrid, produced by crossing the inbred maize line PH87P with another maize plant, and seed and plants produced therefrom. The invention also relates to methods for producing a modified PH87P maize plant that comprises in its genetic material one or more transgenes or backcross conversion genes and to the transgenic and backcross conversion maize plants produced by these methods. This invention also relates to methods for producing other inbred and hybrid maize lines derived from inbred maize line PH87P and to the inbred and hybrid maize lines so produced.

33 Claims, No Drawings

INBRED MAIZE LINE PH87P

CROSS-REFERENCE TO RELATED APPLICATIONS

This application is a continuation of U.S. patent application Ser. No. 10/355,633, now U.S. Pat. No. 6,888,051, filed on Jan. 31, 2003, the contents of which are hereby incorporated by reference in their entirety.

FIELD OF THE INVENTION

This invention relates generally to the field of maize breeding, specifically relating to an inbred maize line designated PH87P.

BACKGROUND OF THE INVENTION

The goal of plant breeding is to combine, in a single variety or hybrid, various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important. Traditional plant breeding is an important tool in developing new and improved commercial crops.

SUMMARY OF THE INVENTION

According to the invention, there is provided a novel inbred maize line, designated PH87P. This invention thus relates to the seeds of inbred maize line PH87P, to the plants of inbred maize line PH87P, to plant parts of inbred maize line PH87P, to methods for producing a maize plant produced by crossing the inbred maize line PH87P with another maize plant, including a plant that is part of a synthetic or natural population, and to methods for producing a maize plant containing in its genetic material one or more backcross conversion trait or transgene and to the backcross conversion maize plants and plant parts produced by those methods. This invention also relates to inbred maize lines and plant parts derived from inbred maize line PH87P, to methods for producing other inbred maize lines derived from inbred maize line PH87P and to the inbred maize lines and their parts derived by the use of those methods. This invention further relates to hybrid maize seeds, plants and plant parts produced by crossing the inbred line PH87P or a backcross conversion of PH87P with another maize line.

DEFINITIONS

Certain definitions used in the specification are provided below. Also in the examples that follow, a number of terms are used herein. In order to provide a clear and consistent understanding of the specification and claims, including the scope to be given such terms, the following definitions are provided. NOTE: ABS is in absolute terms and % MN is percent of the mean for the experiments in which the inbred or hybrid was grown. PCT designates that the trait is calculated as a percentage. % NOT designates the percentage of plants that did not exhibit a trait. For example, STKLDG % NOT is the percentage of plants in a plot that were not stalk lodged. These designators will follow the descriptors to denote how the values are to be interpreted.

ABTSTK=ARTIFICIAL BRITTLE STALK. A count of the number of "snapped" plants per plot following machine snapping. A snapped plant has its stalk completely snapped at a node between the base of the plant and the node above the ear. Expressed as percent of plants that did not snap.

ALLELE. Any of one or more alternative forms of a genetic sequence. Typically, in a diploid cell or organism, the two alleles of a given sequence occupy corresponding loci on a pair of homologous chromosomes.

ANT ROT=ANTHRACNOSE STALK ROT (*Colletotrichum graminicola*). A 1 to 9 visual rating indicating the resistance to Anthracnose Stalk Rot. A higher score indicates a higher resistance.

BACKCROSSING. Process in which a breeder crosses a progeny line back to one of the parental genotypes one or more times.

BARPLT=BARREN PLANTS. The percent of plants per plot that were not barren (lack ears).

BREEDING. The genetic manipulation of living organisms.

BREEDING CROSS. A cross to introduce new genetic material into a plant for the development of a new variety. For example, one could cross plant A with plant B, wherein plant B would be genetically different from plant A. After the breeding cross, the resulting F1 plants could then be selfed or sibbed for one, two, three or more times (F1, F2, F3, etc.) until a new inbred variety is developed. For clarification, such new inbred varieties would be within a pedigree distance of one breeding cross of plants A and B.

BRTSTK=BRITTLE STALKS. This is a measure of the stalk breakage near the time of pollination, and is an indication of whether a hybrid or inbred would snap or break near the time of flowering under severe winds. Data are presented as percentage of plants that did not snap.

CLDTST=COLD TEST. The percent of plants that germinate under cold test conditions.

CLN=CORN LETHAL NECROSIS. Synergistic interaction of maize chlorotic mottle virus (MCMV) in combination with either maize dwarf mosaic virus (MDMV-A or MDMV-B) or wheat streak mosaic virus (WSMV). A 1 to 9 visual rating indicating the resistance to Corn Lethal Necrosis. A higher score indicates a higher resistance.

COMRST=COMMON RUST (*Puccinia sorghi*). A 1 to 9 visual rating indicating the resistance to Common Rust. A higher score indicates a higher resistance.

D/D=DRYDOWN. This represents the relative rate at which a hybrid will reach acceptable harvest moisture compared to other hybrids on a 1 to 9 rating scale. A high score indicates a hybrid that dries relatively fast while a low score indicates a hybrid that dries slowly.

DIPERS=DIPLODIA EAR MOLD SCORES (*Diplodia maydis* and *Diplodia macrospora*). A 1 to 9 visual rating indicating the resistance to Diplodia Ear Mold. A higher score indicates a higher resistance.

DIPROT=DIPLODIA STALK ROT SCORE. Score of stalk rot severity due to Diplodia (*Diplodia maydis*). Expressed as a 1 to 9 score with 9 being highly resistant.

DRPEAR=DROPPED EARS. A measure of the number of dropped ears per plot and represents the percentage of plants that did not drop ears prior to harvest.

D/T=DROUGHT TOLERANCE. This represents a 1 to 9 rating for drought tolerance, and is based on data obtained under stress conditions. A high score indicates good drought tolerance and a low score indicates poor drought tolerance.

EARHT=EAR HEIGHT. The ear height is a measure from the ground to the highest placed developed ear node attachment and is measured in centimeters.

EARMLD=GENERAL EAR MOLD. Visual rating (1 to 9 score) where a "1" is very susceptible and a "9" is very resistant. This is based on overall rating for ear mold of mature ears without determining the specific mold organism, and may not be predictive for a specific ear mold.

EARSZ=EAR SIZE. A 1 to 9 visual rating of ear size. The higher the rating the larger the ear size.

EBTSTK=EARLY BRITTLE STALK. A count of the number of "snapped" plants per plot following severe winds when the corn plant is experiencing very rapid vegetative growth in the V5-V8 stage. Expressed as percent of plants that did not snap.

ECB1LF=EUROPEAN CORN BORER FIRST GENERATION LEAF FEEDING (*Ostrinia nubilalis*). A 1 to 9 visual rating indicating the resistance to preflowering leaf feeding by first generation European Corn Borer. A higher score indicates a higher resistance.

ECB2IT=EUROPEAN CORN BORER SECOND GENERATION INCHES OF TUNNELING (*Ostrinia nubilalis*). Average inches of tunneling per plant in the stalk.

ECB2SC=EUROPEAN CORN BORER SECOND GENERATION (*Ostrinia nubilalis*). A 1 to 9 visual rating indicating post flowering degree of stalk breakage and other evidence of feeding by European Corn Borer, Second Generation. A higher score indicates a higher resistance.

ECBDPE=EUROPEAN CORN BORER DROPPED EARS (*Ostrinia nubilalis*). Dropped ears due to European Corn Borer. Percentage of plants that did not drop ears under second generation corn borer infestation.

EGRWTH=EARLY GROWTH. This is a measure of the relative height and size of a corn seedling at the 2-4 leaf stage of growth. This is a visual rating (1 to 9), with 1 being weak or slow growth, 5 being average growth and 9 being strong growth. Taller plants, wider leaves, more green mass and darker color constitute higher score.

ELITE INBRED. An inbred that contributed desirable qualities when used to produce commercial hybrids. An elite inbred may also be used in further breeding for the purpose of developing further improved varieties.

ERTLDG=EARLY ROOT LODGING. Early root lodging is the percentage of plants that do not root lodge prior to or around anthesis; plants that lean from the vertical axis at an approximately 30° angle or greater would be counted as root lodged.

ERTLPN=EARLY ROOT LODGING. An estimate of the percentage of plants that do not root lodge prior to or around anthesis; plants that lean from the vertical axis at an approximately 30° angle or greater would be considered as root lodged.

ERTLSC=EARLY ROOT LODGING SCORE. Score for severity of plants that lean from a vertical axis at an approximate 30° angle or greater which typically results from strong winds prior to or around flowering recorded within 2 weeks of a wind event. Expressed as a 1 to 9 score with 9 being no lodging.

ESTCNT=EARLY STAND COUNT. This is a measure of the stand establishment in the spring and represents the number of plants that emerge on per plot basis for the inbred or hybrid.

EYESPT=EYE SPOT (*Kabatiella zeae* or *Aureobasidium zeae*). A 1 to 9 visual rating indicating the resistance to Eye Spot. A higher score indicates a higher resistance.

FUSERS=FUSARIUM EAR ROT SCORE (*Fusarium moniliforme* or *Fusarium subglutinans*). A 1 to 9 visual rating indicating the resistance to *Fusarium* ear rot. A higher score indicates a higher resistance.

GDU=GROWING DEGREE UNITS. Using the Barger Heat Unit Theory, which assumes that maize growth occurs in the temperature range 50° F.-86° F. and that temperatures outside this range slow down growth; the maximum daily heat unit accumulation is 36 and the minimum daily heat unit accumulation is 0. The seasonal accumulation of GDU is a major factor in determining maturity zones.

GDUSHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp.})}{2} - 50$$

The highest maximum temperature used is 86° F. and the lowest minimum temperature used is 50° F. For each inbred or hybrid it takes a certain number of GDUs to reach various stages of plant development.

GDUSLK=GDU TO SILK. The number of growing degree units required for an inbred line or hybrid to have approximately 50 percent of the plants with silk emergence from time of planting. Growing degree units are calculated by the Barger Method as given in GDU SHD definition.

GENOTYPE. Refers to the genetic constitution of a cell or organism.

GIBERS=GIBBERELLA EAR ROT (PINK MOLD) (*Gibberella zeae*). A 1 to 9 visual rating indicating the resistance to *Gibberella* Ear Rot. A higher score indicates a higher resistance.

GIBROT=GIBBERELLA STALK ROT SCORE. Score of stalk rot severity due to *Gibberella* (*Gibberella zeae*). Expressed as a 1 to 9 score with 9 being highly resistant.

GLFSPT=GRAY LEAF SPOT (*Cercospora zeae-maydis*). A 1 to 9 visual rating indicating the resistance to Gray Leaf Spot. A higher score indicates a higher resistance.

GOSWLT=GOSS' WILT (*Corynebacterium nebraskense*). A 1 to 9 visual rating indicating the resistance to Goss' Wilt. A higher score indicates a higher resistance.

GRNAPP=GRAIN APPEARANCE. This is a 1 to 9 rating for the general appearance of the shelled grain as it is harvested based on such factors as the color of harvested grain, any mold on the grain, and any cracked grain. High scores indicate good grain quality.

HCBLT=HELMINTHOSPORIUM CARBONUM LEAF BLIGHT (*Helminthosporium carbonum*). A 1 to 9 visual rating indicating the resistance to Helminthosporium infection. A higher score indicates a higher resistance.

HD SMT=HEAD SMUT (*Sphacelotheca reiliana*). This score indicates the percentage of plants not infected.

HSKCVR=HUSK COVER. A 1 to 9 score based on performance relative to key checks, with a score of 1 indicating very short husks, tip of ear and kernels showing; 5 is intermediate coverage of the ear under most conditions, sometimes with thin husk; and a 9 has husks extending and closed beyond the tip of the ear. Scoring can best be done near physiological maturity stage or any time during dry down until harvested.

INC D/A=GROSS INCOME (DOLLARS PER ACRE). Relative income per acre assuming drying costs of two cents per point above 15.5 percent harvest moisture and current market price per bushel.

INCOME/ACRE. Income advantage of hybrid to be patented over other hybrid on per acre basis.

INC ADV=GROSS INCOME ADVANTAGE. GROSS INCOME advantage of variety #1 over variety #2.

KSZDCD=KERNEL SIZE DISCARD. The percent of discard seed; calculated as the sum of discarded tip kernels and extra large kernels.

LINKAGE. Refers to a phenomenon wherein alleles on the same chromosome tend to segregate together more often than expected by chance if their transmission was independent.

LINKAGE DISEQUILIBRIUM. Refers to a phenomenon wherein alleles tend to remain together in linkage groups when segregating from parents to offspring, with a greater frequency than expected from their individual frequencies.

L/POP=YIELD AT LOW DENSITY. Yield ability at relatively low plant densities on a 1 to 9 relative system with a higher number indicating the hybrid responds well to low plant densities for yield relative to other hybrids. A 1, 5, and 9 would represent very poor, average, and very good yield response, respectively, to low plant density.

LRTLDG=LATE ROOT LODGING. Late root lodging is the percentage of plants that do not root lodge after anthesis through harvest; plants that lean from the vertical axis at an approximately 30° angle or greater would be counted as root lodged.

LRTLPN=LATE ROOT LODGING. Late root lodging is an estimate of the percentage of plants that do not root lodge after anthesis through harvest; plants that lean from the vertical axis at an approximately 30° angle or greater would be considered as root lodged.

LRTLSC=LATE ROOT LODGING SCORE. Score for severity of plants that lean from a vertical axis at an approximate 30° angle or greater which typically results from strong winds after flowering. Recorded prior to harvest when a root-lodging event has occurred. This lodging results in plants that are leaned or "lodged" over at the base of the plant and do not straighten or "goose-neck" back to a vertical position. Expressed as a 1 to 9 score with 9 being no lodging.

MDMCPX=MAIZE DWARF MOSAIC COMPLEX (MDMV=Maize Dwarf Mosaic Virus and MCDV=Maize Chlorotic Dwarf Virus). A 1 to 9 visual rating indicating the resistance to Maize Dwarf Mosaic Complex. A higher score indicates a higher resistance.

MST=HARVEST MOISTURE. The moisture is the actual percentage moisture of the grain at harvest.

MSTADV=MOISTURE ADVANTAGE. The moisture advantage of variety #1 over variety #2 as calculated by: MOISTURE of variety #2–MOISTURE of variety #1=MOISTURE ADVANTAGE of variety #1.

NLFBLT=NORTHERN LEAF BLIGHT (*Helminthosporium turcicum* or *Exserohilum turcicum*). A 1 to 9 visual rating indicating the resistance to Northern Leaf Blight. A higher score indicates a higher resistance.

OILT=GRAIN OIL. Absolute value of oil content of the kernel as predicted by Near-Infrared Transmittance and expressed as a percent of dry matter.

PEDIGREE DISTANCE. Relationship among generations based on their ancestral links as evidenced in pedigrees. May be measured by the distance of the pedigree from a given starting point in the ancestry.

PLANT. As used herein, the term "plant" includes reference to an immature or mature whole plant, including a plant that has been detasseled or from which seed or grain has been removed. Seed or embryo that will produce the plant is also considered to be the plant.

PLANT PARTS. As used herein, the term "plant parts" includes leaves, stems, roots, seed, grain, embryo, pollen, ovules, flowers, ears, cobs, husks, stalks, root tips, anthers, silk, tissue, cells and the like.

PLANT CELL. Plant cell, as used herein includes, plant cells whether isolated, in tissue culture or incorporated in a plant or plant part.

PLTHT=PLANT HEIGHT. This is a measure of the height of the plant from the ground to the tip of the tassel in centimeters.

POLSC=POLLEN SCORE. A 1 to 9 visual rating indicating the amount of pollen shed. The higher the score the more pollen shed.

POLWT=POLLEN WEIGHT. This is calculated by dry weight of tassels collected as shedding commences minus dry weight from similar tassels harvested after shedding is complete.

POP K/A=PLANT POPULATIONS. Measured as 1000s per acre.

POP ADV=PLANT POPULATION ADVANTAGE. The plant population advantage of variety #1 over variety #2 as calculated by PLANT POPULATION of variety #2–PLANT POPULATION of variety #1=PLANT POPULATION ADVANTAGE of variety #1.

PRM=PREDICTED RELATIVE MATURITY. This trait, predicted relative maturity, is based on the harvest moisture of the grain. The relative maturity rating is based on a known set of checks and utilizes standard linear regression analyses and is also referred to as the Comparative Relative Maturity Rating System that is similar to the Minnesota Relative Maturity Rating System.

PRMSHD=A relative measure of the growing degree units (GDU) required to reach 50% pollen shed. Relative values are predicted values from the linear regression of observed GDU's on relative maturity of commercial checks.

PROT=GRAIN PROTEIN. Absolute value of protein content of the kernel as predicted by Near-Infrared Transmittance and expressed as a percent of dry matter.

RTLDG=ROOT LODGING. Root lodging is the percentage of plants that do not root lodge; plants that lean from the vertical axis at an approximately 30° angle or greater would be counted as root lodged.

RTLADV=ROOT LODGING ADVANTAGE. The root lodging advantage of variety #1 over variety #2.

SCTGRN=SCATTER GRAIN. A 1 to 9 visual rating indicating the amount of scatter grain (lack of pollination or kernel abortion) on the ear. The higher the score the less scatter grain.

SDGVGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A maize breeder may utilize his or her own set of traits for the selection index. One of the traits that is almost always included is yield. The selection index data presented in the tables represent the mean value averaged across testing stations.

SLFBLT=SOUTHERN LEAF BLIGHT (*Helminthosporium maydis* or *Bipolaris maydis*). A 1 to 9 visual rating indicating the resistance to Southern Leaf Blight. A higher score indicates a higher resistance.

SOURST=SOUTHERN RUST (*Puccinia polysora*). A 1 to 9 visual rating indicating the resistance to Southern Rust. A higher score indicates a higher resistance.

STAGRN=STAY GREEN. Stay green is the measure of plant health near the time of black layer formation (physiological maturity). A high score indicates better late-season plant health.

STDADV=STALK STANDING ADVANTAGE. The advantage of variety #1 over variety #2 for the trait STK CNT.

STKCNT=NUMBER OF PLANTS. This is the final stand or number of plants per plot.

STKLDG=STALK LODGING REGULAR. This is the percentage of plants that did not stalk lodge (stalk breakage) at regular harvest (when grain moisture is between about 20 and 30%) as measured by either natural lodging or pushing the stalks and determining the percentage of plants that break below the ear.

STKLDL=LATE STALK LODGING. This is the percentage of plants that did not stalk lodge (stalk breakage) at or around late season harvest (when grain moisture is between about 15 and 18%) as measured by either natural lodging or pushing the stalks and determining the percentage of plants that break below the ear.

STKLDS=STALK LODGING SCORE. A plant is considered as stalk lodged if the stalk is broken or crimped between the ear and the ground. This can be caused by any or a combination of the following; strong winds late in the season, disease pressure within the stalks, ECB damage or genetically weak stalks. This trait should be taken just prior to or at harvest. Expressed on a 1 to 9 scale with 9 being no lodging.

STLLPN=LATE STALK LODGING. This is the percent of plants that did not stalk lodge (stalk breakage or crimping) at or around late season harvest (when grain moisture is below 20%) as measure by either natural lodging or pushing the stalks and determining the percentage of plants that break or crimp below the ear.

STLPCN=STALK LODGING REGULAR. This is an estimate of the percentage of plants that did not stalk lodge (stalk breakage) at regular harvest (when grain moisture is between about 20 and 30%) as measured by either natural lodging or pushing the stalks and determining the percentage of plants that break below the ear.

STRT=GRAIN STARCH. Absolute value of starch content of the kernel as predicted by Near-infrared Transmittance and expressed as a percent of dry matter.

STWWLT=Stewart's Wilt (*Erwinia stewartii*). A 1 to 9 visual rating indicating the resistance to Stewart's Wilt. A higher score indicates a higher resistance.

TASBLS=TASSEL BLAST. A 1 to 9 visual rating was used to measure the degree of blasting (necrosis due to heat stress) of the tassel at the time of flowering. A 1 would indicate a very high level of blasting at time of flowering, while a 9 would have no tassel blasting.

TASSZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEXEAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data are given as a percentage of tillers: number of tillers per plot divided by number of plants per plot.

TSTWT=TEST WEIGHT (UNADJUSTED). The measure of the weight of the grain in pounds for a given volume (bushel).

TSWADV=TEST WEIGHT ADVANTAGE. The test weight advantage of variety #1 over variety #2.

WIN M %=PERCENT MOISTURE WINS.

WIN Y %=PERCENT YIELD WINS.

YIELD BU/A=YIELD (BUSHELS/ACRE). Yield of the grain at harvest in bushels per acre adjusted to 15% moisture.

YLDADV=YIELD ADVANTAGE. The yield advantage of variety #1 over variety #2 as calculated by: YIELD of variety #1−YIELD variety #2=yield advantage of variety #1.

YLDSC=YIELD SCORE. A 1 to 9 visual rating was used to give a relative rating for yield based on plot ear piles. The higher the rating the greater visual yield appearance.

Definitions for Area of Adaptability

When referring to area of adaptability, such term is used to describe the location with the environmental conditions that would be well suited for this maize line. Area of adaptability is based on a number of factors, for example: days to maturity, insect resistance, disease resistance, and drought resistance. Area of adaptability does not indicate that the maize line will grow in every location within the area of adaptability or that it will not grow outside the area.

Central Corn Belt: Iowa, Illinois, Indiana

Drylands: non-irrigated areas of North Dakota, South Dakota, Nebraska, Kansas, Colorado and Oklahoma Eastern U.S.: Ohio, Pennsylvania, Delaware, Maryland, Virginia, and West Virginia North central U.S.: Minnesota and Wisconsin Northeast: Michigan, New York, Vermont, and Ontario and Quebec Canada Northwest U.S.: North Dakota, South Dakota, Wyoming, Washington, Oregon, Montana, Utah, and Idaho South central U.S.: Missouri, Tennessee, Kentucky, Arkansas Southeast U.S.: North Carolina, South Carolina, Georgia, Florida, Alabama, Mississippi, and Louisiana Southwest U.S.: Texas, Oklahoma, New Mexico, Arizona Western U.S.: Nebraska, Kansas, Colorado, and California Maritime Europe France, Germany, Belgium and Austria

DETAILED DESCRIPTION OF THE INVENTION

All tables discussed in the Detailed Description of the Invention section can be found at the end of the section.

Morphological and Physiological Characteristics of PH87P

Inbred maize line PH87P is a yellow, flint-dent maize inbred that is best suited to be used as a male in the production of the first generation F1 maize hybrids. Inbred maize line PH87P is best adapted to the Central Corn Belt, Southcentral, Southeastern, and Western areas of the United States, and can be used to produce hybrids with approximately 112 maturity based on the Comparative Relative Maturity Rating System for harvest moisture of grain. Inbred maize line PH87P demonstrates good pollen production, small seed, high test weight, and good ear mold tolerance as an inbred per se. In hybrid combination, inbred PH87P demonstrates high yield potential, good gray leaf spot and *Fusarium* ear mold tolerance, and below average ear and plant height.

The inbred has shown uniformity and stability within the limits of environmental influence for all the traits as described in the Variety Description Information (Table 1, found at the end of the section). The inbred has been self-pollinated and ear-rowed a sufficient number of generations with careful attention paid to uniformity of plant type to ensure the homozygosity and phenotypic stability necessary for use in commercial hybrid seed production. The line has been increased both by hand and in isolated fields with continued observation for uniformity. No variant traits have been observed or are expected in PH87P.

Inbred maize line PH87P, being substantially homozygous, can be reproduced by planting seeds of the line, growing the resulting maize plants under self-pollinating or sib-pollinating conditions with adequate isolation, and harvesting the resulting seed using techniques familiar to the agricultural arts.

Genetic Marker Profile

To select and develop superior inbred parental lines for producing hybrids, it is necessary to identify and select genetically unique individuals that occur in a segregating population. The segregating population is the result of a combination of crossover events plus the independent assortment of specific combinations of alleles at many gene loci that results in specific and unique genotypes. The genetic variation among individual progeny of a breeding cross allows for the identification of rare and valuable new genotypes. Once identified, it is possible to utilize routine and predictable breeding methods to develop progeny that retain the rare and valuable new genotypes developed by the initial breeder.

Even if the entire genotypes of the parents of the breeding cross were characterized and a desired genotype known, only a few if any individuals having the desired genotype may be found in a large segregating F2 population. It would be very unlikely that a breeder of ordinary skill in the art would be able to recreate the same line twice from the very same original parents as the breeder is unable to direct how the genomes combine or how they will interact with the environmental conditions. This unpredictability results in the expenditure of large amounts of research resources in the development of a superior new maize inbred line. Once such a line is developed its value to society is substantial since it is important to advance the germplasm base as a whole in order to maintain or improve traits such as yield, disease resistance, pest resistance and plant performance in extreme weather conditions. Backcross trait conversions are routinely used to add or modify one or a few traits of such a line and this further enhances its value and usefulness to society.

Phenotypic traits exhibited by PH87P can be used to characterize the genetic contribution of PH87P to progeny lines developed through the use of PH87P. Quantitative traits including, but not limited to, yield, maturity, stay green, root lodging, stalk lodging, and early growth are typically governed by multiple genes at multiple loci. PH87P progeny plants that retain the same degree of phenotypic expression of these quantitative traits as PH87P have received significant genotypic and phenotypic contribution from PH87P. This characterization is enhanced when such quantitative trait is not exhibited in non-PH87P breeding material used to developed the PH87P progeny.

In addition to phenotypic observations, a plant can also be identified by its genotype. The genotype of a plant can be characterized through a genetic marker profile, which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Berry, Don, et al., "Assessing Probability of Ancestry Using Simple Sequence Repeat Profiles Applications to Maize Hybrids and Inbreds", Genetics, 2002, 161:813-824, which is incorporated by reference herein.

Particular markers used for these purposes are not limited to the set of markers disclosed herein, but are envisioned to include any type of marker and marker profile which provides a means of distinguishing varieties. In addition to being used for identification of Inbred Line PH87P, a hybrid produced through the use of PH87P, and the identification or verification of pedigree for progeny plants produced through the use of PH87P, the genetic marker profile is also useful in further breeding and in developing backcross conversions.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR™ detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by gel electrophoresis of the amplification products. Scoring of marker genotype is based on the size of the amplified fragment as measured by molecular weight (MW) rounded to the nearest integer. While variation in the primer used or in laboratory procedures can affect the reported molecular weight, relative values should remain constant regardless of the specific primer or laboratory used. When comparing lines it is preferable if all SSR profiles are performed in the same lab. The SSR analyses reported herein were conducted in-house at Pioneer Hi-Bred. An SSR service is available to the public on a contractual basis by Paragen (formerly Celera AgGen) in Research Triangle Park, North Carolina.

Primers used for the SSRs reported herein are publicly available and may be found in the Maize GDB using the World Wide Web prefix followed by maizegdb.org (maintained by the USDA Agricultural Research Service), in Sharopova et al. (Plant Mol. Biol. 48(5-6):463-481), Lee et al. (Plant Mol. Biol. 48(5-6); 453-461), or may be constructed from sequences if reported herein. Some marker information may be available from Paragen.

Map information is provided by bin number as reported in the Maize GDB. The bin number digits to the left of decimal point represent the chromosome on which such marker is located, and the digits to the right of the decimal represent the location on such chromosome. Any bin numbers reported in parenthesis represent other bin locations for such marker that have been reported in the literature or on the Maize GDB. A bin number.xx designation indicates that the bin location on that chromosome is not known. Map positions are also available on the Maize GDB for a variety of different mapping populations.

The SSR profile of Inbred PH87P can be found in Table 2 found at the end of this section. The profile can be used to identify hybrids comprising PH87P as a parent, since such hybrids will comprise two sets of allele, one set of which will be the same alleles as PH87P. Because an inbred is essentially homozygous at all relevant loci, an inbred should, in almost all cases, have only one allele at each locus. In contrast, a genetic marker profile of a hybrid should be the sum of those parents, e.g., if one inbred parent had allele x at a particular locus, and the other inbred parent had allele y the hybrid is x.y (heterozygous) by inference. Subsequent generations of progeny produced by selection and breeding are expected to be of genotype x (homozygous), y (homozygous), or x.y (heterozygous) for that locus position. When the F1 plant is used to produce an inbred, the inbred should be either x or y for that allele.

Plants and plant parts substantially benefiting from the use of PH87P in their development such as PH87P comprising a backcross conversion, transgene, or genetic sterility factor, may be identified by having a molecular marker profile with a high percent identity to PH87P.

The SSR profile of PH87P also can be used to identify essentially derived varieties and other progeny lines developed from the use of PH87P, as well as cells and other plant parts thereof. Progeny plants and plant parts produced using PH87P may be identified by having a molecular marker profile of at least 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from inbred line PH87P.

Unique SSR Profiles

While determining the SSR genetic marker profile of the inbreds described supra, several unique SSR profile loci sets were or may be identified through further analysis which did not appear in either parent of such inbred.

Such unique SSR profiles may arise during the breeding process from recombination or mutation. A combination of several unique alleles provides a means of identifying an inbred, a hybrid produced from such inbred, and progeny produced from such inbred. Such progeny may be further characterized as being within a pedigree distance of PH87P, such as within 1, 2, 3, 4 or 5 or less breeding crosses to a maize plant other than PH87P or a plant that has PH87P as a parent or other progenitor. Further unique molecular profiles may be identified with other molecular tools such as SNPs and RFLPs.

Each genetic marker profile represents a novel grouping of alleles unique to an inbred. Each of the unique SSR profiles that may be found are referred to as a "loci set".

Comparing PH87P to Other Inbreds

A breeder uses various methods to help determine which plants should be selected from the segregating populations and ultimately which inbred lines will be used to develop hybrids for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which inbred lines and hybrid combinations are significantly better or different for one or more traits of interest. Experimental design methods are used to assess error so that differences between two inbred lines or two hybrid lines can be more accurately determined. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding would know how to evaluate the traits of two plant varieties to determine if there is no significant difference between the two traits expressed by those varieties. For example, see Fehr, Walt, Principles of Cultivar Development, p. 261-286 (1987) which is incorporated herein by reference. Mean trait values may be used to determine whether trait differences are significant, and preferably the traits are measured on plants grown under the same environmental conditions.

In Tables 3A-3F, data from traits and characteristics of inbred maize line PH87P per se are given and compared to other maize inbred lines.

Inbred by Tester comparisons are also used to evaluate two inbreds. Combined inbred by tester comparison results can be used to distinguish two inbred lines while also providing information about the combining ability of the inbreds used.

Tables 4A-4D compare PH87P to four other inbreds, when each inbred is crossed to the same tester lines.

Methods of Introducing a New Gene or Trait into PH87P.

Field crops are bred through techniques that take advantage of the plant's method of pollination. A plant is self-pollinated if pollen from one flower is transferred to the same or another flower of the same plant. A plant is sib-pollinated when individuals within the same family or line are used for pollination. A plant is cross-pollinated if the pollen comes from a flower on a different plant from a different family or line. The terms "cross-pollination" and "out-cross" as used herein do not include self-pollination or sib-pollination.

Maize (zea mays L.), often referred to as corn in the United States, can be to bred by both self-pollination and cross-pollination techniques. Maize has separate male and female flowers on the same plant, located on the tassel and the ear, respectively. Natural or open pollination occurs in maize when wind blows pollen from the tassels to the silks that protrude from the tops of the ears.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants; each heterozygous at a number of gene loci, will produce a population of hybrid plants that differ genetically and will not be uniform.

One possible method of introducing a new gene or trait into PH87P is producing a backcross conversion of PH87P. A backcross conversion occurs when DNA sequences are introduced through traditional (non-transformation) breeding techniques, such as backcrossing (Hallauer et al., 1988). DNA sequences, whether naturally occurring or transgenes, may be introduced using these traditional breeding techniques. A backcross conversion may produce a plant with a trait conversion in at least one or more crosses, including at least 2 crosses, at least 3 crosses, at least 4 crosses, and the like. Molecular marker assisted breeding or selection may be utilized to reduce the number of backcrosses necessary to achieve the backcross conversion. The term backcross conversion is also referred to in the art as a single locus conversion. Reference is made to US 2002/0062506A1 for a detailed discussion of single locus conversions and traits that may be incorporated into PH87P through backcross conversion. Desired traits transferred through this process include, but are not limited to, waxy starch, grain color, nutritional enhancements, altered fatty acid profile, increased digestibility, low phytate, industrial enhancements, disease resistance, insect resistance, herbicide resistance and yield enhancements. The trait of interest is transferred from the donor parent to the recurrent parent, in this case, the maize plant disclosed herein. The backcross conversion may result from either the transfer of a dominant allele or a recessive allele. Selection of progeny containing the trait of interest is accomplished by direct selection for a trait associated with a dominant allele. Selection of progeny for a trait that is transferred via a recessive allele, such as the waxy starch characteristic, requires growing and selfing the first backcross generation to determine which plants carry the recessive alleles. Recessive traits may require additional progeny testing in successive backcross generations to determine the presence of the gene of interest. Along with selection for the trait of interest, progeny are selected for the phenotype of the recurrent parent. While occasionally additional polynucleotide sequences or genes are transferred along with the backcross conversion, this is an insubstantial change to the variety, and backcross conversion lines are easily developed without undue experimentation. Hallauer et al. (1998, page 472) states that "For single gene traits that are relatively easy to classify, the backcross method is effective and relatively easy to manage." Poehlman et al. (1995, page 334) states that "A backcross-derived inbred line fits into the same hybrid combination as the recurrent parent inbred line and contributes the effect of the additional gene added through the backcross."

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species that are inserted into the genome using transformation are referred to herein collectively as "transgenes". A transformed plant may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention, in particular embodiments, also relates to transformed versions of the claimed inbred maize line PH87P as well as hybrid combinations thereof.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999). In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into a particular maize plant using transformation techniques, could be moved into another line using traditional breeding techniques that are well known in the plant breeding arts. For example, a backcrossing approach is commonly used to move a transgene from a transformed maize plant to an elite inbred line, and the resulting progeny would then comprise the transgene(s). Also, if an inbred line was used for the transformation then the transgenic plants could be crossed to a different inbred in order to produce a transgenic hybrid maize plant. As used herein, "crossing" can refer to a simple X by Y cross, or the process of backcrossing, depending on the context.

Various genetic elements can be introduced into the plant genome using transformation. These elements include but are not limited to genes; coding sequences; inducible, constitutive, and tissue specific promoters; enhancing sequences; and signal and targeting sequences. See the traits, genes and transforming methods listed in U.S. Pat. No. 6,118,055, which are herein incorporated by reference.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981). One embodiment, the biomass of interest is seed.

A genetic map can be generated, primarily via conventional Restriction Fragment Length Polymorphisms (RFLP), Polymerase Chain Reaction (PCR) analysis, and Simple Sequence Repeats (SSR) and Single Nucleotide Polymorphisms (SNP) which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269-284 (CRC Press, Boca Raton, 1993).

Wang et al. discuss "Large Scale Identification, Mapping and Genotyping of Single-Nucleotide Polymorphisms in the Human Genome", Science, 280:1077-1082, 1998, and similar capabilities are becoming increasingly available for the corn genome. Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques. SNP's may also be used alone or in combination with other techniques.

Likewise, by means of the present invention, plants can be genetically engineered to express various phenotypes of agronomic interest. Through the transformation of maize the expression of genes can be modulated to enhance disease resistance, insect resistance, herbicide resistance, agronomic traits as well as grain quality traits. Transformation can also be used to insert DNA sequences which control or help control male-sterility. DNA sequences native to maize as well as non-native DNA sequences can be transformed into maize and used to modulate levels of native or non-native proteins. Anti-sense technology, various promoters, targeting sequences, enhancing sequences, and other DNA sequences can be inserted into the maize genome for the purpose of modulating the expression of proteins. Exemplary transgenes implicated in this regard include, but are not limited to, those categorized below.

1. Transgenes that Confer Resistance to Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78: 1089 (1994) (*Arabidopsis* RSP2 gene for resistance to *Pseudomonas syringae*). A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and hereby are incorporated by reference for this purpose: U.S. Pat. Nos. 5,188,960; 5,689,052; 5,880,275; and WO 97/40162.

(C) A lectin. See, for example, the disclosure by Van Damme et al., *Plant Molec. Biol.* 24:25 (1994), who disclose the nucleotide sequences of several *Clivia miniata* mannose-binding lectin genes.

(D) A vitamin-binding protein such as avidin. See PCT Application US93/06487 the contents of which are hereby incorporated by reference for this purpose. The application teaches the use of avidin and avidin homologues as larvicides against insect pests.

(E) An enzyme inhibitor, for example, a protease inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), and Sumitani et al., *Biosci. Biotech. Biochem.* 57:1243 (1993) (nucleotide sequence of *Streptomyces nitrosporeus* α-amylase inhibitor) and U.S. Pat. No. 5,494,813.

(F) An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

(G) An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

(H) An insect-specific venom produced in nature by a snake, a wasp, etc. For example, see Pang et al., *Gene* 116:165 (1992), for disclosure of heterologous expression in plants of a gene coding for a scorpion insectotoxic peptide.

(I) An enzyme responsible for an hyperaccumulation of a monterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT Application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

(K) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104:1467 (1994), who provide the nucleotide sequence of a maize calmodulin cDNA clone.

(L) A hydrophobic moment peptide. See PCT Application WO95/16776 (disclosure of peptide derivatives of Tachyplesin which inhibit fungal plant pathogens) and PCT Application WO95/18855 (teaches synthetic antimicrobial peptides that confer disease resistance), the respective contents of which are hereby incorporated by reference for this purpose.

(M) A membrane permease, a channel former or a channel blocker. For example, see the disclosure by Jaynes et al., *Plant Sci.* 89:43 (1993), of heterologous expression of a cecropin-β lytic peptide analog to render transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(O) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(P) A virus-specific antibody. See, for example, Tavladoraki et al., *Nature* 366:469 (1993), who show that transgenic plants expressing recombinant antibody genes are protected from virus attack.

(Q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

(R) A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

(S) Genes involved in the Systemic Acquired Resistance (SAR) Response and/or the pathogenesis related genes. Briggs, S., Current Biology, 5(2) (1995).

(T) Antifungal genes (Cornelissen and Melchers, P I. Physiol. 101:709-712, (1993) and Parijs et al., Planta 183: 258-264, (1991) and Bushnell et al., Can. J. of Plant Path. 20(2):137-149 (1998).

2. Transgenes that Confer Resistance to a Herbicide, for Example:

(A) A herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international Publication WO 96/33270, which are incorporated herein by reference for this purpose.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international Publications WO 97/04103; WO 97/04114; WO 00/66746; WO 01/66704; WO 00/66747 and WO 00/66748, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. Application Ser. Nos. 60/244,385; 60/377,175 and 60/377,719. A DNA molecule encoding a mutant aroA gene can be obtained under ATCC Accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Patent Nos. 0 242 246 and 0 242 236 to Leemans et al. De Greef et al, *Bio/Technology* 7:61 (1989), describe the production of transgenic plants that express chimeric bar genes coding for phosphinothricin acetyl transferase activity. See also, U.S. Pat. Nos. 5,969, 213; 5,489,520; 5,550,318; 5,874,265; 5,919,675; 5,561, 236; 5,648,477; 5,646,024; 6,177,616 B1; and 5,879,903, which are incorporated herein by reference for this purpose. Exemplary of genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83:435 (1992).

(C) A herbicide that inhibits photosynthesis, such as a triazine (psbA and gs+ genes) and a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

(D) Acetohydroxy acid synthase, which has been found to make plants that express this enzyme resistant to multiple types of herbicides, has been introduced into a variety of plants (see, e.g., Hattori et al. (1995) Mol. Gen. Genet. 246:419). Other genes that confer tolerance to herbicides include: a gene encoding a chimeric protein of rat cytochrome P4507A1 and yeast NADPH-cytochrome P450 oxidoreductase (Shiota et al. (1994) Plant Physiol 106:17), genes for glutathione reductase and superoxide dismutase (Aono et al. (1995) Plant Cell Physiol. 36:1687, and genes for various phosphotransferases (Datta et al. (1992) Plant Mol. Biol. 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international Publication WO 01/12825, which are incorporated herein by reference for this purpose.

3. Transgenes that Confer or Contribute to a Grain Trait, Such as:

(A) Modified fatty acid metabolism, for example, by transforming a plant with an antisense gene of stearoyl-ACP desaturase to increase stearic acid content of the plant. See Knultzon et al., *Proc. Natl. Acad. Sci. USA* 89:2624 (1992).

(B) Decreased Phytate Content
(1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene.
(2) A gene could be introduced that reduces phytate content. In maize, this, for example, could be accomplished, by cloning and then re-introducing DNA associated with the single allele which is responsible for maize mutants characterized by low levels of phytic acid. See Raboy et al., *Maydica* 35:383 (1990).

(C) Modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus mutans* fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10:292 (1992) (production of transgenic plants that express *Bacillus licheniformis* α-amylase), Elliot et al., *Plant Molec. Biol.* 21:515 (1993) (nucleotide sequences of tomato invertase genes), Søgaard et al., *J. Biol. Chem.* 268: 22480 (1993) (site-directed mutagenesis of barley α-amylase gene), and Fisher et al., *Plant Physiol.* 102:1045 (1993) (maize endosperm starch branching enzyme II).

(D) Elevated oleic acid via FAD-2 gene modification and/or decreased linolenic acid via FAD-3 gene modification (see U.S. Pat. Nos. 6,063,947; 6,323,392; and WO 93/11245).

4. Genes that Control Male-sterility
(A) Introduction of a deacetylase gene under the control of a tapetum-specific promoter and with the application of the chemical N-Ac-PPT (WO 01/29237).
(B) Introduction of various stamen-specific promoters (WO 92/13956, WO 92/13957).
(C) Introduction of the barnase and the barstar gene (Paul et al. Plant Mol. Biol. 19:611-622, 1992).

PH87P Inbreds that are Male Sterile

Hybrid seed production requires elimination or inactivation of pollen produced by the female inbred parent. Incomplete removal or inactivation of the pollen provides the potential for self-pollination. A reliable method of controlling male fertility in plants offers the opportunity for improved plant breeding. This is especially true for development of maize hybrids, which relies upon some sort of male sterility system. It should be understood that PH87P can be produced in a male-sterile form. There are several ways in which a maize plant can be manipulated so that it is male sterile. These include use of manual or mechanical emasculation (or detasseling), use of one or more genetic factors that confer male sterility, including cytoplasmic genetic and/or nuclear genetic male sterility, use of gametocides and the like. A male sterile inbred designated PH87P may include one or more genetic factors, which result in cytoplasmic genetic and/or nuclear genetic male sterility. Such embodiments are also within the scope of the present claims. The term manipulated to be male sterile refers to the use of any available techniques to produce a male sterile version of maize line PH87P. The male sterility may be either partial or complete male sterility.

Hybrid maize seed is often produced by a male sterility system incorporating manual or mechanical detasseling. Alternate strips of two maize inbreds are planted in a field, and the pollen-bearing tassels are removed from one of the inbreds (female). Provided that there is sufficient isolation from sources of foreign maize pollen, the ears of the detasseled inbred will be fertilized only from the other inbred (male), and the resulting seed is therefore hybrid and will form hybrid plants.

The laborious detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile, and either option may be preferred depending on the intended use of the hybrid. The same hybrid seed, a portion produced from detasseled fertile maize and a portion produced using the CMS system, can be blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., of Pioneer Hi-Bred, U.S. Pat. No. 5,432,068, have developed a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

These and the other methods of conferring genetic male sterility in the art, each possess their own benefits and drawbacks. Some other methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 Publication No. 329,308 and PCT Application PCT/CA90/00037 published as WO 90/08828).

Another system for controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904). Application of the gametocide, timing of the application and genotype specificity often limit the usefulness of the approach and it is not appropriate in all situations.

Incomplete control over male fertility may result in self-pollinated seed being unintentionally harvested and packaged with hybrid seed. The male parent is grown next to the female parent in the field, so there is the very low probability that the male selfed seed could be unintentionally harvested and packaged with the hybrid seed. Once the seed from the hybrid bag is planted, it is possible to identify and select these self-pollinated plants. These self-pollinated plants will be genetically equivalent to one of the inbred lines used to produce the hybrid. Though the possibility of inbreds being included hybrid seed bags exists, the occurrence is very low because much care is taken to avoid such inclusions. It is worth noting that hybrid seed is sold to growers for the production of grain or forage and not for breeding or seed production.

These self-pollinated plants can be identified and selected by one skilled in the art due to their decreased vigor when compared to the hybrid. Inbreds are identified by their less vigorous appearance for vegetative and/or reproductive characteristics, including shorter plant height, small ear size, ear and kernel shape, cob color, or other characteristics.

Identification of these self-pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pp. 1-8 (1995), the disclosure of which is expressly incorporated herein by reference. Through these technologies, the homozygosity of the self pollinated line can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritica si Aplicata Vol. 20(1) p. 29-42.

Development of Maize Hybrids Using PH87P

A single cross maize hybrid results from the cross of two inbred lines, each of which has a genotype that complements the genotype of the other. The hybrid progeny of the first generation is designated F1. In the development of commercial hybrids in a maize plant breeding program, only the F1 hybrid plants are sought. F1 hybrids are more vigorous than their inbred parents. This hybrid vigor, or heterosis, can be manifested in many polygenic traits, including increased vegetative growth and increased yield.

PH87P may be used to produce hybrid maize seed. One such embodiment is the method of crossing inbred maize line PH87P with another maize plant, such as a different maize inbred line, to form a first generation F1 hybrid plant. The first generation F1 hybrid plant produced by this method is also an embodiment of the invention. This first generation F1 plant will comprise an essentially complete set of the alleles of inbred line PH87P. One of ordinary skill in the art can utilize either breeder books or molecular methods to identify a particular F1 hybrid plant produced using inbred line PH87P, and any such individual plant is also encompassed by this invention. These embodiments also cover use of these methods with transgenic, male sterile and/or backcross conversions of inbred line PH87P.

The development of a maize hybrid in a maize plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in maize, the vigor of the lines decreases. Vigor is restored when two different inbred lines are crossed to produce the hybrid. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

PH87P may be used to produce a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced from hybrids is not used for planting stock.

Inbred by Tester Comparisons

Combining ability of a line, as well as the performance of the line per se is a factor in the selection of improved maize inbreds. Combining ability refers to a line's contribution as a parent when crossed with other lines to form hybrids. The hybrids formed for the purpose of selecting superior lines are designated as test crosses. One way of measuring combining ability is by using values based in part on the overall mean of a number of test crosses. This mean may be adjusted to remove environmental effects and it is adjusted for known genetic relationships among the lines.

Combining Ability Data

A general combining ability report for inbred PH87P is provided in Table 5.

Table 5 shows overall mean values of traits from numerous F1 lines produced by crosses between inbred PH87P and other maize lines. Table 5 demonstrates that inbred PH87P shows good general combining ability for hybrid production.

A specific combining ability report for inbred PH87P is provided in Tables 5A and 5B. Tables 5A and 5B show mean values of traits from numerous individual F1 lines produced by crosses between inbred PH87P and other maize lines.

Hybrid Comparisons

The results in Tables 6A-6F compare two hybrids for which inbred PH87P is a parent and three other hybrids.

Using PH87P to Develop Other Maize Inbreds

Inbred maize lines are typically developed for use in the production of hybrid maize lines. However, PH87P could also be used to derive new maize inbred lines. Inbred maize lines preferably should be highly homogeneous, substantially homozygous and reproducible to be useful as parents of commercial hybrids. Plant breeding techniques known in the art and used in a maize plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of maize hybrids in a maize plant breeding program requires, in general, the development of homozygous inbred lines, the crossing of these lines, and the evaluation of the crosses. There are many analytical methods available to evaluate the result of a cross. The oldest and most traditional method of analysis is the observation of phenotypic traits. Alternatively, the genotype of a plant can be examined.

Using PH87P in a Breeding Program

This invention is directed to methods for producing a maize plant by crossing a first parent maize plant with a second parent maize plant wherein either the first or second parent maize plant is an inbred maize plant of the line PH87P. Thus, any such methods using the inbred maize line PH87P are part of this invention: selfing, sibbing, backcrosses, mass selection, bulk selection, hybrid production, crosses to populations, and the like. All plants produced using inbred maize line PH87P as a parent are within the scope of this invention, including plants essentially derived from inbred maize line PH87P, as such term is defined in 7 U.S.C. § 2104(a)(3) of the Plant Variety Protection Act, which definition is hereby incorporated by reference. This also includes progeny plants and parts thereof with at least one ancestor that is PH87P, and more specifically, where the pedigree of the progeny includes 1, 2, 3, 4, and/or 5 or less breeding crosses to a maize plant other than PH87P or a plant that has PH87P as a parent or other progenitor. All breeders of ordinary skill in the art maintain pedigree records of their breeding programs. These pedigree records contain a detailed description of the breeding process, including a listing of all parental lines used in the breeding process and information on how such line was used. Thus, a breeder would know if PH87P were used in the development of a progeny line, and would also know how many crosses to a line other than PH87P or line with PH87P as a parent or other progenitor were made in the development of any progeny line. The inbred maize line may also be used in crosses with other, different, maize inbreds to produce first generation (F1) maize hybrid seeds and plants with superior characteristics.

Pedigree Breeding

Pedigree breeding starts with the crossing of two genotypes, such as PH87P and one other elite inbred line having one or more desirable characteristics that is lacking or which complements PH87P. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→F$_5$, etc. After a sufficient amount of inbreeding, successive filial generations will serve to increase seed of the developed inbred. Preferably, an inbred-line comprises homozygous alleles at about 95% or more of its loci.

Backcrossing

In addition to being used to create a backcross conversion, backcrossing can also be used to modify PH87P and a hybrid that is made using the modified PH87P. As discussed previously, backcrossing can be used to transfer a specific desirable trait from one line, the donor parent, to an inbred called the recurrent parent which has overall good agronomic characteristics yet lacks that desirable trait. This transfer of the desirable trait into an inbred with overall good agronomic characteristics can be accomplished by first crossing a recurrent parent and a donor parent (non-recurrent parent). The progeny of this cross is then mated back to the recurrent parent followed by selection in the resultant progeny for the desired trait to be transferred from the non-recurrent parent as well as selection for the characteristics of the recurrent parent. Typically after four or more backcross generations with selection for the desired trait and the characteristics of the recurrent parent, the progeny will contain essentially all genes of the recurrent parent except for the genes controlling the desired trait. However, the number of backcross generations can be less if molecular markers are used during selection or elite germplasm is used as the donor parent. The last backcross generation is then selfed to give pure breeding progeny for the gene(s) being transferred. In addition to the above described use, backcrossing can be used in conjunction with pedigree breeding to develop new inbred lines. For example, an F1 can be created that is backcrossed to one of its parent lines to create a BC1, BC2, BC3, etc. Progeny are selfed and selected so that the newly developed inbred has many of the attributes of the recurrent parent and some of the desired attributes of the non-recurrent parent. This approach leverages the value and strengths of the recurrent parent for use in new hybrids and breeding, and has very significant value for a breeder.

Recurrent Selection and Mass Selection

Recurrent selection is a method used in a plant breeding program to improve a population of plants. PH87P can be used in a recurrent selection program to improve the population. The method entails individual plants cross pollinating with each other to form progeny which are then grown. The superior progeny are then selected by any number of methods, which include individual plant, half-sib progeny, full-sib progeny, selfed progeny and topcrossing. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds. Mass selection is a useful technique when used in conjunction with molecular marker enhanced selection. In mass selection seeds from individuals are selected based on phenotype. These selected seeds are then bulked and used to grow the next generation. Similarly, bulk selection requires growing a population of plants in a bulk plot, allowing the plants to self-pollinate, harvesting the seed in bulk and then using a sample of the seed harvested in bulk to plant the next generation. Also, instead of directed pollination, open pollination could be used as part of the breeding program.

Mutation Breeding

Mutation breeding is one of many methods that could be used to introduce new traits into PH87P. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in "Principals of Cultivar Development" Fehr, 1993 Macmillan Publishing Company the disclosure of which is incorporated herein by reference.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing PH87P.

Isozyme Electrophoresis and RFLPs as discussed in Lee, M., "Inbred Lines of Maize and Their Molecular Markers," *The Maize Handbook*, (Springer-Verlag, New York, Inc. 1994, at 423-432) incorporated herein by reference for this purpose, have been widely used to determine genetic composition. Isozyme Electrophoresis has a relatively low number of available markers and a low number of allelic variants among maize inbreds. RFLPs allow more discrimination because they have a higher degree of allelic variation in maize and a larger number of markers can be found. Both of these methods have been eclipsed by SSRs as discussed in Smith et al., "An evaluation of the utility of SSR loci as molecular markers in maize (*Zea mays* L.): comparisons with data from RFLPs and pedigree", *Theoretical and Applied Genetics* (1997) vol. 95 at 163-173 and by Pejic et al., "Comparative analysis of genetic similarity among maize inbreds detected by RFLPs, RAPDs, SSRs, and AFLPs," *Theoretical and Applied Genetics* (1998) at 1248-1255 incorporated herein by reference. SSR technology is more efficient and practical to use than RFLPs; more marker loci can be routinely used and more alleles per marker locus can be found using SSRs in comparison to RFLPs. Single Nucleotide Polymorphisms may also be used to identify the unique genetic composition of the invention and progeny lines retaining that unique genetic composition. Various molecular marker techniques may be used in combination to enhance overall resolution.

Maize DNA molecular marker linkage maps have been rapidly constructed and widely implemented in genetic studies. One such study is described in Boppenmaier, et al., "Comparisons among strains of inbreds for RFLPs", Maize Genetics Cooperative Newsletter, 65:1991, pg. 90, is incorporated herein by reference.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection.

Production of Double Haploids

The production of double haploids can also be used for the development of inbreds in the breeding program. An F1 hybrid for which PH87P is a parent can be used to produce double haploid plants. Double haploids are produced by the doubling of a set of chromosomes (1 N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetics, 77:889-892, 1989. This can be advantageous because the process omits the generations of selfing needed to obtain a homozygous plant from a heterozygous source.

Use of PH87P in Tissue Culture

This invention is also directed to the use of PH87P in tissue culture. As used herein, the term "tissue culture" includes plant protoplasts, plant cell tissue culture, cultured microspores, plant calli, plant clumps, and the like. As used herein, phrases such as "growing the seed" or "grown from the seed" include embryo rescue, isolation of cells from seed for use in tissue culture, as well as traditional growing methods.

Duncan, Williams, Zehr, and Widholm, Planta (1985) 165:322-332 reflects that 97% of the plants cultured that produced callus were capable of plant regeneration. Subsequent experiments with both inbreds and hybrids produced 91% regenerable callus that produced plants. In a further study in 1988, Songstad, Duncan & Widholm in *Plant Cell Reports* (1988), 7:262-265 reports several media additions that enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter,* 60:64-65 (1986), refers to somatic embryogenesis from glume callus cultures and B. V. Conger, et al., *Plant Cell Reports,* 6:345-347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize, including tassel/anther culture, is described in U.S. 2002/0062506A1 and European Patent Application, Publication No. 160,390, each of which are incorporated herein by reference for this purpose. Maize tissue culture procedures are also described in Green and Rhodes, "Plant Regeneration in Tissue Culture of Maize," *Maize for Biological Research* (Plant Molecular Biology Association, Charlottesville, Virginia 1982, at 367-372) and in Duncan, et al., "The Production of Callus Capable of Plant Regeneration from Immature Embryos of Numerous *Zea Mays* Genotypes," 165 *Planta* 322-332 (1985). Thus, another aspect of this invention is to provide cells which upon growth and differentiation produce maize plants having the genotype and/or physiological and morphological characteristics of inbred line PH87P.

Progeny of the breeding methods described herein may be characterized in any number of ways, such as by traits retained in the progeny, pedigree and/or molecular markers. Using the breeding methods described herein, one can develop individual plants, plant cells, and populations of plants that retain at least 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from inbred line PH87P. In pedigree analysis the percentage genetic contribution may not be actually known, but on average 50% of the starting germplasm would be expected to be passed to the progeny line after one cross to another line, 25% after another cross to a different line, and so on. With backcrossing, the expected contribution of PH87P after 2, 3, 4 and 5 doses (or 1, 2, 3 and 4 backcrosses) would be 75%, 87.5%, 93.75% and 96.875% respectively. Actual genetic contribution may be much higher than the genetic contribution expected by pedigree, especially if molecular markers are used in selection. Molecular markers could also be used to confirm and/or determine the pedigree of the progeny line.

Specific methods and products produced using inbred line PH87P in plant breeding are discussed in the following sections. The methods outlined are described in detail by way of illustration and example for purposes of clarity and understanding. However, it will be obvious that certain changes and modifications may be practiced within the scope of the invention.

One method for producing a line derived from inbred line PH87P is as follows. One of ordinary skill in the art would produce or obtain a seed from the cross between inbred line PH87P and another variety of maize, such as an elite inbred variety. The F1 seed derived from this cross would be grown to form a homogeneous population. The F1 seed would contain essentially all of the alleles from variety PH87P and essentially all of the alleles from the other maize variety. The F1 nuclear genome would be made-up of 50% variety PH87P and 50% of the other elite variety. The F1 seed would be grown and allowed to self, thereby forming F2 seed. On average the F2 seed would have derived 50% of its alleles from variety PH87P and 50% from the other maize variety, but many individual plants from the population would have a greater percentage of their alleles derived from PH87P (Wang J. and R. Bernardo, 2000, Crop Sci. 40:659-665 and Bernardo, R. and A. L. Kahler, 2001, Theor. Appl. Genet. 102:986-992). The molecular markers of PH87P could be used to select and retain those lines with high similarity to PH87P. The F2 seed would be grown and selection of plants would be made based on visual observation, markers and/or measurement of traits. The traits used for selection may be any PH87P trait described in this specification, including the inbred per se maize PH87P traits described herein under the detailed description of inbred PH87P. Such traits may also be the good general or specific combining ability of PH87P, including its ability to produce hybrids with the approximate maturity and/or hybrid combination traits described herein in under the detailed description of inbred PH87P. The PH87P progeny plants that exhibit one or more of the desired PH87P traits, such as those listed herein, would be selected and each plant would be harvested separately. This F3 seed from each plant would be grown in individual rows and allowed to self. Then selected rows or plants from the rows would be harvested individually. The selections would again be based on visual observation, markers and/or measurements for desirable traits of the plants, such as one or more of the desirable PH87P traits listed herein. The process of growing and selection would be repeated any number of times until a PH87P progeny inbred plant is obtained. The PH87P progeny inbred plant would contain desirable traits derived from inbred plant PH87P, some of which may not have been expressed by the other maize variety to which inbred line PH87P was crossed and some of which may have been expressed by both maize varieties but now would be at a level equal to or greater than the level expressed in inbred variety PH87P. However, in each case the resulting progeny line would benefit from the efforts of the inventor(s), and would not have existed but for the inventor(s) work in creating PH87P. The PH87P progeny inbred plants would have, on average, 50% of their nuclear genes derived from inbred line PH87P, but many individual plants from the population would have a greater percentage of their alleles derived from PH87P. This breeding cycle, of crossing and selfing, and optional selection, may be repeated to produce another population of PH87P progeny maize plants with, on average, 25% of their nuclear genes derived from inbred line PH87P, but, again, many individual plants from the population would have a greater percentage of their alleles derived from PH87P. Another embodiment of the invention is a PH87P progeny plant that has received the desirable PH87P traits listed herein through the use of PH87P, which traits were not exhibited by other plants used in the breeding process.

The previous example can be modified in numerous ways, for instance selection may or may not occur at every selfing generation, selection may occur before or after the actual self-pollination process occurs, or individual selections may be made by harvesting individual ears, plants, rows or plots at any point during the breeding process described. In addition, double haploid breeding methods may be used at any step in the process. The population of plants produced at each and any cycle of breeding is also an embodiment of the invention, and on average each such population would predictably consist of plants containing approximately 50% of its genes from inbred line PH87P in the first breeding cycle, 25% of its genes from inbred line PH87P in the second breeding cycle, 12.5% of its genes from inbred line PH87P in the third breeding cycle and so on. However, in each case the use of PH87P provides a substantial benefit. The linkage groups of PH87P would be retained in the progeny lines, and since current estimates of the maize genome size is about 50,000-80,000 genes (Xiaowu, Gai et al., Nucleic Acids Research, 2000, Vol. 28, No. 1, 94-96), in addition to non-coding DNA that impacts gene expression, it provides a significant advantage to use PH87P as starting material to produce a line that retains desired genetics or traits of PH87P.

Another embodiment of this invention is the method of obtaining a substantially homozygous PH87P progeny plant by obtaining a seed from the cross of PH87P and another maize plant and applying double haploid methods to the F1 seed or F1 plant or to any successive filial generation. Such methods decrease the number of generations required to produce an inbred with similar genetics or characteristics to PH87P. See Bernardo, R. and Kahler, A. L., Theor. Appl. Genet. 102:986-992, 2001.

The utility of inbred maize line PH87P also extends to crosses with other species. Commonly, suitable species will be of the family Graminaceae, and especially of the genera *Zea, Tripsacum, Coix, Schlerachne, Polytoca, Chionachne*, and *Trilobachne*, of the tribe Maydeae. Potentially suitable for crosses with PH87P may be the various varieties of grain sorghum, *Sorghum bicolor* (L.) Moench.

As is readily apparent to one skilled in the art, the foregoing are only some of the various ways by which the inbred can be obtained by those looking to use the germplasm. Other means are available, and the above examples are illustrative only.

INDUSTRIAL APPLICABILITY

Maize is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Plant parts other than the grain of maize are also used in industry: for example, stalks and husks are made into paper and wallboard and cobs are used for fuel and to make charcoal.

The seed of inbred maize line PH87P, the plant produced from the inbred seed, the hybrid maize plant produced from the crossing of the inbred, hybrid seed, and various parts of the hybrid maize plant and transgenic versions of the foregoing, can be utilized for human food, livestock feed, and as a raw material in industry.

DEPOSITS

Applicants have made a deposit of at least 2500 seeds of Inbred Maize Line PH87P with the American Type Culture Collection (ATCC), Manassas, Va. 20110 USA, ATCC Deposit No. PTA-4879. The seeds deposited with the ATCC on Dec. 26, 2002 were taken from the deposit maintained by Pioneer Hi-Bred International, Inc., 800 Capital Square, 400 Locust Street, Des Moines, Iowa 50309-2340 since prior to the filing date of this application. Access to this deposit will be available during the pendency of the application to the Commissioner of Patents and Trademarks and persons determined by the Commissioner to be entitled thereto upon request. Upon allowance of any claims in the application, the Applicants will make the deposit available to the public pursuant to 37 C.F.R. § 1.808. This deposit of the Inbred Maize Line PH87P will be maintained in the ATCC depository, which is a public depository, for a period of 30 years, or 5 years after the most recent request, or for the enforceable life of the patent, whichever is longer, and will be replaced if it becomes nonviable during that period. Additionally, Applicants have satisfied all the requirements of 37 C.F.R. §§ 1.801-1.809, including providing an indication of the viability of the sample upon deposit. Applicants have no authority to waive any restrictions imposed by law on the transfer of biological material or its transportation in commerce. Applicants do not waive any infringement of his rights granted under this patent or under the Plant Variety Protection Act (7 USC 2321 et seq). U.S. Plant Variety Protection of Inbred Maize Line PH87P has been applied for under Application No. 200300236.

TABLE 1

VARIETY DESCRIPTION INFORMATION
PH87P

| | | Avg. | Sta. Dev | Sam. Size |
|---|---|---|---|---|
| 1. TYPE: (Describe intermediate types in comments section) | | | | |
| 1 = Sweet, 2 = Dent, 3 = Flint, 4 = Flour, 5 = Pop and 6 = Ornamental. Comments: Flint-Dent | | 2.5 | | |
| 2. MATURITY: DAYS HEAT UNITS | Days | H. Units | | |
| From emergence to 50% of plants in silk | 67 | 1,531 | | |
| From emergence to 50% of plants in pollen | 65 | 1,468 | | |
| From 10% to 90% pollen shed | 1 | 40 | | |
| From 50% Silk to harvest at 25% moisture | | | | |
| 3. PLANT: | | | | |
| Plant Height (to tassel tip) (cm) | | 230.5 | 17.35 | 30 |
| Ear Height (to base of top ear node) (cm) | | 64.3 | 10.38 | 30 |
| Length of Top Ear Internode (cm) | | 14.8 | 2.41 | 30 |
| Average Number of Tillers per Plant | | 0.0 | 0.03 | 6 |
| Average Number of Ears per Stalk | | 1.0 | 0.07 | 6 |
| Anthocyanin of Brace Roots: 1 = Absent, 2 = Faint, 3 = Moderate, 4 = Dark | | 3 | | |
| 4. LEAF: | | | | |
| Width of Ear Node Leaf (cm) | | 10.2 | 0.91 | 30 |
| Length of Ear Node Leaf (cm) | | 81.9 | 4.68 | 30 |
| Number of Leaves above Top Ear | | 7.6 | 0.72 | 30 |
| Leaf Angle: (measure from 2nd leaf above ear at anthesis to stalk above leaf)(Degrees) | | 30.2 | 7.24 | 30 |
| *Leaf color: Dark Green Munsell code: 7.5GY34 | | | | |
| Leaf Sheath Pubescence: 1 = none to 9 = like peach fuzz | | 2 | | |
| 5. TASSEL: | | | | |
| Number of Primary Lateral Branches | | 10.4 | 2.55 | 30 |
| Branch Angle from Central Spike | | 21.0 | 5.41 | 30 |
| Tassel Length (from top leaf collar to tassel tip)(cm): | | 61.3 | 6.00 | 30 |
| Pollen Shed: 0 = male sterile, 9 = heavy shed | | 7 | | |
| *Anther Color: Yellow Munsell code: 5Y88 | | | | |
| *Glume Color: Light Green Munsell code: 5GY46 | | | | |
| *Bar Glumes (glume bands): 1 = absent, 2 = present | | 1 | | |
| Peduncle Length (from top leaf to basal branches) (cm): | | 22.9 | 5.12 | 30 |
| 6a. EAR (Unhusked ear) | | | | |
| *Silk color: Pink Munsell c. 7.5R76 (3 days after silk emergence) | | | | |
| *Fresh husk color: Light Green Munsell c. 5GY68 (25 days after 50% silking) | | | | |
| *Dry husk color: Buff Munsell c. 5Y92 (65 days after 50% silking) | | | | |
| Ear position at dry husk stage: 1 = upright, 2 = horizontal, 3 = pendant | | 1 | | |
| Husk tightness: (1 = very loose, 9 = very tight) | | 5 | | |
| Husk extension (at harvest): 1 = short(ears exposed), 2 = medium (<8 cm), 3 = long (8-10 cm), 4 = v. long (>10 cm) | | 2 | | |
| 6b. EAR (Husked ear data) | | | | |
| Ear length (cm): | | 16.6 | 1.75 | 30 |
| Ear diameter at mid-point (mm) | | 41.2 | 2.10 | 30 |
| Ear weight (gm): | | 131.7 | 29.47 | 30 |

TABLE 1-continued

VARIETY DESCRIPTION INFORMATION
PH87P

| | | | |
|---|---|---|---|
| Number of Kernel Rows: | 15.9 | 1.17 | 30 |
| Kernel Rows: 1 = indistinct, 2 = distinct | 2 | | |
| Row alignment: 1 = straight, 2 = slightly curved, 3 = spiral | 2 | | |
| Shank Length (cm): | 12.0 | 4.90 | 30 |
| Ear Taper: 1 = slight cylind., 2 = average, 3 = extreme conic. | 2 | | |

7. KERNEL (Dried):

| | | | |
|---|---|---|---|
| Kernel Length (mm): | 10.5 | 0.82 | 30 |
| Kernel Width (mm): | 7.4 | 0.63 | 30 |
| Kernel Thickness (mm): | 4.3 | 0.45 | 30 |
| Round Kernels (shape grade) (%) | 37.9 | 10.22 | 6 |
| Aleurone Color pattern: 1 = homozygous, 2 = segregating | 1 | | |
| *Aleurone Color: Yellow Munsell c.: 10YR714 | | | |
| *Hard Endo. color: Yellow Munsell c.: 10YR712 | | | |
| Endosperm Type: | 3 | | |
| 1 = sweet (su1), 2 = extra sweet (sh2), | | | |
| 3 = normal starch, 4 = high amylose starch, | | | |
| 5 = waxy starch, 6 = high protein, | | | |
| 7 = high lysine, 8 = super sweet (se), | | | |
| 9 = high oil, 10 = other | | | |
| Weight per 100 kernels (unsized sample) (gm): | 26.0 | 2.83 | 6 |

8. COB:

| | | | |
|---|---|---|---|
| *Cob Diameter at mid-point (mm): | 24.3 | 1.62 | 30 |
| *Cob Color: Red Munsell c.: 10R48 | | | |

10. DISEASE RESISTANCE:
(Rate from 1 = most-susceptable to 9 = most-resistant. Leave blank if not tested, leave race or strain options blank if polygenic.)
  A. LEAF BLIGHTS, WILTS, AND LOCAL INFECTION DISEASES
    Anthracnose Leaf Blight (*Colletotrichum graminicola*)
    Common Rust (*Puccinia sorghi*)
    Common Smut (*Ustilago maydis*)
    Eyespot (*Kabatiella zeae*)
    Gross's Wilt (*Clavibacter michiganense* spp. *nebraskense*)
    Gray Leaf Spot (*Cercospora zeae-maydis*)
    Helminthosporium Leaf Spot (*Bipolaris zeicola*) Race:
    Northern Leaf Blight (*Exserohilum turcicum*) Race:
    Southern Leaf Blight (*Bipolaris maydis*) Race:
    Southern Rust (*Puccinia polysora*)
    Stewart's Wilt (*Erwinia stewartii*)
    Other (Specify):_____
  B. SYSTEMIC DISEASES
    Corn Lethal Necrosis (MCMV and MDMV)
    Head Smut (*Sphacelotheca reiliana*)
    Maize Chlorotic Dwarf Virus (MDV)
    Maize Chlorotic Mottle Virus (MCMV)
    Maize Dwarf Mosaic Virus (MDMV)
    Sorghum Downy Mildew of Corn (*Peronosclerospora sorghi*)
    Other (Specify):_____
  C. STALK ROTS
    Anthracnose Stalk Rot (*Colletotrichum graminicola*)
    Diploidia Stalk Rot (*Stenocarpella maydis*)
    Fusarium Stalk Rot (*Fusarium moniliforme*)
    Gibberella Stalk Rot (*Gibberella zeae*)
    Other (Specify):_____
  D. EAR AND KERNEL ROTS
    *Aspergillus* Ear and Kernel Rot (*Aspergillus flavus*)
    Diplodia Ear Rot (*Stenocarpella maydis*)
    *Fusarium* Ear and Kernel Rot (*Fusarium moniliforme*)
    Gibberella Ear Rot (*Gibberella zeae*)
    Other (Specify):_____

11. INSECT RESISTANCE:
(Rate from 1 = most-suscept. to 9 = most-resist., leave blank if not tested.)
  Corn Worm (*Helicoverpa zea*)
    Leaf Feeding
    Silk Feeding
    Ear Damage
  Corn Leaf Aphid (*Rophalosiphum maydis*)
  Corn Sap Beetle (*Capophilus dimidiatus*)
  European Corn Borer (*Ostrinia nubilalis*)
    1st. Generation (Typically whorl leaf feeding)
    2nd. Generation (Typically leaf sheath-collar feeding)
    Stalk Tunneling
    cm tunneled/plant
  Fall armyworm (*Spodoptera fruqiperda*)
    Leaf Feeding
    Silk Feeding
    mg larval wt.
  Maize Weevil (*Sitophilus zeamaize*)
  Northern Rootworm (*Diabrotica barberi*)
  Southern Rootworm (*Diabrotica undecimpunctata*)
  Southwestern Corn Borer (*Diatreaea grandiosella*)
    Leaf Feeding
    Stalk Tunneling
    cm tunneled/plant
  Two-spotted Spider Mite (*Tetranychus utricae*)
  Western Rootworm (*Diabrotica virgifrea virgifrera*)
  Other (Specify):_____

12. AGRONOMIC TRAITS:
  Staygreen (at 65 days after anthesis; rate from 1-worst to 9-excellent)
  % Dropped Ears (at 65 days after anthesis)
  % Pre-anthesis Brittle Snapping
  % Pre-anthesis Root Lodging
  % Post-anthesis Root Lodging (at 65 days after anthesis)
  % Post-anthesis Stalk Lodging
  Kg/ha Yield of inbred per se (at 12-13% grain moisture)

*Munsell Glossy Book of Color, a standard color reference Kollmorgen Inst. Corp. New Windsor NY.

TABLE 2

SSR PROFILE OF PH87P

| Locus | Bin # | PH87P mwt |
|---|---|---|
| bnlg1014 | 1.01 | 126 |
| phi427913 | 1.01 | 132 |
| phi056 | 1.01 | 252 |
| bnlg1127 | 1.02 | 119 |
| bnlg1007 | 1.02 | 137 |
| bnlg1083 | 1.02 | 206 |
| bnlg1627 | 1.02 | 208 |
| bnlg1429 | 1.02 | 213 |
| bnlg1953 | 1.02 | 255 |
| bnlg439 | 1.03 | 235 |
| phi109275 | 1.03 | 135 |
| bnlg1484 | 1.03 | 146 |
| phi339017 | 1.03 | 148 |
| bnlg1203 | 1.03 | 307 |
| dupssr26 | 1.04 | 127 |
| bnlg2238 | 1.04 | 207 |
| bnlg2086 | 1.04 | 221 |
| bnlg1016 | 1.04 | 259 |
| bnlg1886 | 1.05 | 142 |
| bnlg1832 | 1.05 | 218 |
| bnlg1884 | 1.05 | 274 |
| bnlg1615 | 1.06 | 223 |
| bnlg1057 | 1.06 | 251 |
| bnlg1556 | 1.07 | 211 |
| phi423298 | 1.08 | 129 |
| bnlg2228 | 1.08 | 228 |
| phi323065 | 1.08 | 331 |
| phi002 | 1.08 | 72 |
| phi335539 | 1.08 | 91 |
| bnlg1331 | 1.09 | 124 |
| phi011 | 1.09 | 230 |
| bnlg1720 | 1.09(1.10) | 244 |
| phi308707 | 1.10 | 134 |
| phi265454 | 1.11 | 221 |
| phi260485 | 1.11 | 288 |
| phi227562 | 1.11 | 322 |
| phi064 | 1.11 | 87 |
| bnlg1130 | 1.XX | 175 |
| bnlg2031 | 1.XX | 214 |
| phi402893 | 2.00 | 221 |
| phi96100 | 2.01 | 283 |

TABLE 2-continued

SSR PROFILE OF PH87P

| Locus | Bin # | PH87P mwt |
|---|---|---|
| bnlg1017 | 2.02 | 197 |
| bnlg1327 | 2.02 | 276 |
| bnlg2277 | 2.02 | 296 |
| bnlg1537 | 2.03 | 120 |
| phi109642 | 2.03 | 142 |
| bnlg1064 | 2.03 | 191 |
| phi083 | 2.04 | 126 |
| bnlg1018 | 2.04 | 142 |
| bnlg1909 | 2.05 | 298 |
| bnlg1396 | 2.06 | 136 |
| bnlg1831 | 2.06 | 194 |
| bnlg1036 | 2.06 | 195 |
| bnlg1138 | 2.06 | 227 |
| phi251315 | 2.07 | 127 |
| phi328189 | 2.08 | 124 |
| phi127 | 2.08 | 124 |
| phi427434 | 2.08 | 133 |
| phi090 | 2.08 | 141 |
| bnlg1141 | 2.08 | 155 |
| phi435417 | 2.08 | 216 |
| bnlg2237 | 2.08 | 219 |
| bnlg1258 | 2.08 | 221 |
| bnlg1940 | 2.08 | 251 |
| bnlg1520 | 2.09 | 289 |
| phi101049 | 2.10 | 234 |
| bnlg1690 | 2.XX | 128 |
| phi453121 | 3.00 | 214 |
| phi104127 | 3.01 | 165 |
| phi404206 | 3.01 | 305 |
| bnlg1144 | 3.02 | 116 |
| phi193225 | 3.02 | 137 |
| bnlg1647 | 3.02 | 166 |
| phi374118 | 3.02 | 227 |
| bnlg1523 | 3.03 | 267 |
| bnlg1452 | 3.04 | 128 |
| bnlg1113 | 3.04 | 137 |
| phi029 | 3.04 | 154 |
| bnlg1019 | 3.04 | 158 |
| bnlg1816 | 3.04 | 286 |
| bnlg1035 | 3.05 | 104 |
| phi053 | 3.05 | 169 |
| phi073 | 3.05 | 194 |
| bnlg2241 | 3.06 | 119 |
| bnlg1951 | 3.06 | 130 |
| phi102228 | 3.06 | 139 |
| bnlg1160 | 3.06 | 225 |
| bnlg1496 | 3.09 | 220 |
| phi072 | 4.00(4.01) | 163 |
| phi295450 | 4.01 | 187 |
| phi213984 | 4.01 | 287 |
| bnlg1162 | 4.03 | 107 |
| phi021 | 4.03 | 120 |
| phi308090 | 4.04 | 220 |
| phi096 | 4.04 | 238 |
| phi079 | 4.05 | 181 |
| phi438301 | 4.05 | 210 |
| bnlg1265 | 4.05 | 216 |
| bnlg1755 | 4.05 | 220 |
| phi026 | 4.05 | 79 |
| bnlg1937 | 4.05(4.06) | 230 |
| bnlg1137 | 4.06 | 135 |
| umc2038 | 4.07 | 125 |
| bnlg1189 | 4.07 | 133 |
| bnlg1784 | 4.07 | 229 |
| bnlg2244 | 4.08 | 202 |
| phi093 | 4.08 | 284 |
| phi076 | 4.11 | 161 |
| bnlg1890 | 4.11 | 252 |
| phi396160 | 5.02 | 300 |
| phi109188 | 5.03 | 170 |
| bnlg653 | 5.04 | 154 |
| bnlg1208 | 5.04 | 121 |
| phi330507 | 5.04 | 135 |
| phi331888 | 5.04 | 136 |
| bnlg1892 | 5.04 | 160 |
| bnlg2323 | 5.04 | 212 |
| phi333597 | 5.05 | 216 |
| phi085 | 5.06 | 251 |
| bnlg1346 | 5.07 | 178 |
| bnlg1711 | 5.07 | 181 |
| bnlg1118 | 5.07 | 84 |
| bnlg1597 | 5.08 | 216 |
| phi423796 | 6.01 | 131 |
| bnlg1422 | 6.01 | 220 |
| phi389203 | 6.03 | 307 |
| phi452693 | 6.04 | 133 |
| phi445613 | 6.05 | 102 |
| bnlg1174 | 6.05 | 222 |
| umc1413 | 6.05 | 303 |
| umc1463 | 6.06 | 303 |
| phi299852 | 6.07 | 123 |
| phi364545 | 6.07 | 138 |
| bnlg1759 | 6.07 | 151 |
| bnlg1740 | 6.07 | 212 |
| phi070 | 6.07 | 84 |
| phi338882 | 6.XX | 169 |
| bnlg2132 | 7.00 | 203 |
| umc1159 | 7.01 | 233 |
| phi034 | 7.02 | 141 |
| bnlg1094 | 7.02 | 148 |
| bnlg1292 | 7.03 | 141 |
| bnlg1070 | 7.03 | 163 |
| bnlg2271 | 7.03 | 223 |
| phi328175 | 7.04 | 124 |
| phi051 | 7.05 | 140 |
| phi069 | 7.05 | 197 |
| phi116 | 7.06 | 172 |
| phi420701 | 8.00 | 294 |
| bnlg1194 | 8.02 | 196 |
| phi121 | 8.03 | 101 |
| phi100175 | 8.03 | 148 |
| bnlg2082 | 8.03 | 174 |
| bnlg1863 | 8.03 | 247 |
| phi115 | 8.03 | 304 |
| bnlg2046 | 8.04 | 321 |
| bnlg1176 | 8.05 | 221 |
| bnlg1152 | 8.06 | 124 |
| bnlg1031 | 8.06 | 293 |
| bnlg1828 | 8.07 | 171 |
| bnlg1065 | 8.07 | 230 |
| bnlg1056 | 8.08 | 109 |
| phi015 | 8.08 | 85 |
| phi233376 | 8.09 | 151 |
| bnlg1810 | 9.01 | 208 |
| bnlg2122 | 9.01 | 222 |
| phi033 | 9.01 | 261 |
| umc1037 | 9.02 | 218 |
| bnlg1159 | 9.04 | 151 |
| bnlg1012 | 9.04 | 173 |
| phi032 | 9.04 | 241 |
| phi236654 | 9.05 | 120 |
| phi108411 | 9.05 | 129 |
| phi448880 | 9.06(9.07) | 187 |
| bnlg1375 | 9.07 | 168 |
| bnlg1129 | 9.08 | 301 |
| phi059 | 10.02 | 156 |
| phi96342 | 10.02 | 256 |
| bnlg1655 | 10.03 | 151 |
| bnlg1079 | 10.03 | 173 |
| bnlg1655 | 10.03 | 207 |
| bnlg1037 | 10.03 | 311 |
| phi050 | 10.03 | 86 |
| phi301654 | 10.04 | 132 |
| phi062 | 10.04 | 164 |
| phi323152 | 10.05 | 137 |
| bnlg1074 | 10.05 | 180 |
| bnlg1028 | 10.06 | 141 |
| bnlg1185 | 10.07 | 154 |
| bnlg1450 | 10.07 | 192 |

TABLE 3A

PAIRED INBRED COMPARISON REPORT
Variety #1: PH87P
Variety #2: PHR03

| Stat | EGRWTH SCORE ABS | ESTCNT COUNT ABS | TILLER PCT ABS | GDUSHD GDU ABS | GDUSLK GDU ABS | POLWT VALUE ABS | POLWT VALUE % MN |
|---|---|---|---|---|---|---|---|
| Mean1 | 5.5 | 21.4 | 9.1 | 148.6 | 153.1 | 205.4 | 115.2 |
| Mean2 | 5.6 | 19.2 | 2.8 | 152.1 | 156.6 | 223.4 | 124.3 |
| Locs | 27 | 18 | 20 | 53 | 54 | 5 | 5 |
| Reps | 27 | 18 | 20 | 53 | 54 | 10 | 10 |
| Diff | −0.1 | 2.3 | −6.3 | −3.5 | −3.5 | −18.0 | −9.1 |
| Prob | 0.691 | 0.002 | 0.072 | 0.000 | 0.000 | 0.534 | 0.568 |

| Stat | TASBLS SCORE ABS | TASSZ SCORE ABS | PLTHT CM ABS | EARHT CM ABS | STAGRN SCORE ABS | STKLDG % NOT ABS | SCTGRN SCORE ABS |
|---|---|---|---|---|---|---|---|
| Mean1 | 9.0 | 6.1 | 234.1 | 80.3 | 6.3 | 100.0 | 7.6 |
| Mean2 | 8.5 | 6.0 | 230.1 | 84.3 | 4.6 | 100.0 | 7.0 |
| Locs | 6 | 42 | 42 | 5 | 11 | 3 | 11 |
| Reps | 6 | 42 | 42 | 5 | 11 | 3 | 11 |
| Diff | 0.5 | 0.2 | 4.1 | −4.1 | 1.6 | 0.0 | 0.6 |
| Prob | 0.363 | 0.291 | 0.126 | 0.577 | 0.018 | 1.000 | 0.111 |

| Stat | EARSZ SCORE ABS | TEXEAR SCORE ABS | EARMLD SCORE ABS | BARPLT % NOT ABS | GLFSPT SCORE ABS | NLFBLT SCORE ABS | SLFBLT SCORE ABS |
|---|---|---|---|---|---|---|---|
| Mean1 | 5.0 | 7.8 | 7.3 | 96.0 | 6.1 | 5.8 | 6.7 |
| Mean2 | 5.7 | 7.4 | 7.6 | 97.4 | 5.0 | 5.0 | 4.6 |
| Locs | 3 | 5 | 7 | 24 | 15 | 6 | 7 |
| Reps | 3 | 5 | 7 | 25 | 23 | 12 | 11 |
| Diff | −0.7 | 0.4 | −0.3 | −1.4 | 1.1 | 0.8 | 2.1 |
| Prob | 0.529 | 0.178 | 0.457 | 0.341 | 0.001 | 0.017 | 0.002 |

| Stat | ANTROT SCORE ABS | MDMCPX SCORE ABS | FUSERS SCORE ABS | DIPERS SCORE ABS | COMRST SCORE ABS | SOURST SCORE ABS | ECB1LF SCORE ABS |
|---|---|---|---|---|---|---|---|
| Mean1 | 4.0 | 2.0 | 5.4 | 4.4 | 6.2 | 2.0 | 7.0 |
| Mean2 | 3.3 | 2.8 | 6.3 | 4.8 | 5.7 | 2.0 | 7.0 |
| Locs | 8 | 3 | 18 | 4 | 7 | 2 | 1 |
| Reps | 15 | 6 | 24 | 6 | 9 | 2 | 2 |
| Diff | 0.7 | −0.8 | −0.9 | −0.4 | 0.5 | 0.0 | 0.0 |
| Prob | 0.252 | 0.038 | 0.002 | 0.718 | 0.412 | 1.000 | |

| Stat | ECB2SC SCORE ABS | HD SMT % NOT ABS | ERTLDG % NOT ABS | ERTLPN % NOT ABS |
|---|---|---|---|---|
| Mean1 | 4.0 | 97.3 | 65.0 | 90.0 |
| Mean2 | 4.0 | 99.3 | 59.1 | 59.5 |
| Locs | 1 | 3 | 1 | 2 |
| Reps | 2 | 6 | 1 | 2 |
| Diff | 0.0 | −2.0 | 5.9 | 30.5 |
| Prob | | 0.221 | | 0.489 |

TABLE 3B

PAIRED INBRED COMPARISON REPORT
Variety #1: PH87P
Variety #2: PH1CA

| Stat | YIELD BU/A 56# ABS | YIELD BU/A 56# % MN | MST PCT ABS | EGRWTH SCORE ABS | ESTCNT COUNT ABS | TILLER PCT ABS |
|---|---|---|---|---|---|---|
| Mean1 | 179.6 | 156.0 | 24.2 | 5.7 | 21.3 | 8.9 |
| Mean2 | 113.1 | 94.6 | 23.4 | 5.7 | 21.8 | 4.4 |
| Locs | 4 | 4 | 4 | 29 | 23 | 25 |
| Reps | 8 | 8 | 8 | 29 | 23 | 25 |
| Diff | 66.5 | 61.3 | −0.8 | 0.0 | −0.6 | −4.5 |
| Prob | 0.023 | 0.040 | 0.292 | 0.851 | 0.178 | 0.161 |

TABLE 3B-continued

PAIRED INBRED COMPARISON REPORT
Variety #1: PH87P
Variety #2: PH1CA

| Stat | GDUSHD GDU ABS | GDUSLK GDU ABS | POLWT VALUE ABS | POLWT VALUE % MN | TASBLS SCORE ABS | TASSZ SCORE ABS |
|---|---|---|---|---|---|---|
| Mean1 | 147.7 | 152.2 | 177.4 | 115.2 | 9.0 | 6.2 |
| Mean2 | 146.2 | 148.9 | 232.7 | 140.7 | 8.9 | 6.3 |
| Locs | 61 | 62 | 17 | 17 | 7 | 51 |
| Reps | 61 | 62 | 33 | 33 | 7 | 51 |
| Diff | 1.5 | 3.3 | −55.3 | −25.5 | 0.1 | −0.1 |
| Prob | 0.002 | 0.000 | 0.012 | 0.087 | 0.356 | 0.644 |

| Stat | PLTHT CM ABS | EARHT CM ABS | STAGRN SCORE ABS | STKLDG % NOT ABS | SCTGRN SCORE ABS | EARSZ SCORE ABS |
|---|---|---|---|---|---|---|
| Mean1 | 235.5 | 79.8 | 6.4 | 100.0 | 7.6 | 5.0 |
| Mean2 | 228.3 | 87.9 | 3.1 | 100.0 | 8.2 | 4.7 |
| Locs | 52 | 5 | 15 | 4 | 17 | 3 |
| Reps | 52 | 5 | 15 | 4 | 17 | 3 |
| Diff | 7.2 | −8.1 | 3.3 | 0.0 | −0.6 | 0.3 |
| Prob | 0.001 | 0.266 | 0.000 | 1.000 | 0.046 | 0.423 |

| Stat | TEXEAR SCORE ABS | EARMLD SCORE ABS | BARPLT % NOT ABS | GLFSPT SCORE ABS | NLFBLT SCORE ABS | SLFBLT SCORE ABS |
|---|---|---|---|---|---|---|
| Mean1 | 7.7 | 7.1 | 95.2 | 6.5 | 5.7 | 6.9 |
| Mean2 | 7.7 | 7.8 | 95.9 | 5.3 | 5.0 | 4.5 |
| Locs | 7 | 10 | 32 | 12 | 5 | 6 |
| Reps | 7 | 10 | 33 | 19 | 10 | 9 |
| Diff | 0.0 | −0.7 | −0.6 | 1.2 | 0.7 | 2.4 |
| Prob | 1.000 | 0.066 | 0.758 | 0.000 | 0.184 | 0.002 |

| Stat | ANTROT SCORE ABS | MDMCPX SCORE ABS | FUSERS SCORE ABS | GIBERS SCORE ABS | DIPERS SCORE ABS | COMRST SCORE ABS |
|---|---|---|---|---|---|---|
| Mean1 | 4.0 | 2.0 | 5.7 | 9.0 | 4.4 | 6.3 |
| Mean2 | 2.4 | 2.8 | 6.5 | 9.0 | 5.3 | 6.0 |
| Locs | 6 | 3 | 19 | 1 | 4 | 8 |
| Reps | 12 | 6 | 24 | 1 | 7 | 10 |
| Diff | 1.6 | −0.8 | −0.8 | 0.0 | −0.9 | 0.3 |
| Prob | 0.023 | 0.130 | 0.005 | | 0.102 | 0.472 |

| Stat | SOURST SCORE ABS | ECB1LF SCORE ABS | ECB2SC SCORE ABS | CLDTST PCT ABS | CLDTST PCT % MN | KSZDCD PCT ABS |
|---|---|---|---|---|---|---|
| Mean1 | 2.0 | 7.0 | 4.0 | 94.5 | 102.8 | 12.3 |
| Mean2 | 2.0 | 7.5 | 2.0 | 93.8 | 102.1 | 26.8 |
| Locs | 2 | 1 | 1 | 4 | 4 | 4 |
| Reps | 2 | 2 | 2 | 4 | 4 | 4 |
| Diff | 0.0 | −0.5 | 2.0 | 0.8 | 0.8 | −14.5 |
| Prob | 1.000 | | | 0.768 | 0.783 | 0.198 |

| Stat | HD SMT % NOT ABS | ERTLDG % NOT ABS | ERTLPN % NOT ABS |
|---|---|---|---|
| Mean1 | 97.3 | 65.0 | 95.0 |
| Mean2 | 89.9 | 88.0 | 85.0 |
| Locs | 3 | 1 | 2 |
| Reps | 6 | 1 | 2 |
| Diff | 7.4 | −23.0 | 10.0 |
| Prob | 0.314 | | 0.500 |

TABLE 3C

PAIRED INBRED COMPARISON REPORT
Variety #1: PH87P
Variety #2: PH21T

| Stat | YIELD BU/A 56# ABS | YIELD BU/A 56# % MN | MST PCT ABS | EGRWTH SCORE ABS | ESTCNT COUNT ABS | TILLER PCT ABS | GDUSHD GDU ABS | GDUSLK GDU ABS | POLWT VALUE ABS | POLWT VALUE % MN |
|---|---|---|---|---|---|---|---|---|---|---|
| Mean1 | 164.2 | 139.9 | 23.8 | 5.7 | 22.6 | 7.8 | 148.9 | 153.5 | 192.5 | 122.4 |
| Mean2 | 142.7 | 121.5 | 23.8 | 5.8 | 23.2 | 1.2 | 150.1 | 152.4 | 127.4 | 77.6 |
| Locs | 8 | 8 | 8 | 36 | 30 | 28 | 92 | 92 | 39 | 39 |
| Reps | 15 | 15 | 15 | 36 | 30 | 28 | 92 | 92 | 71 | 71 |
| Diff | 21.5 | 18.4 | 0.0 | −0.1 | −0.6 | −6.6 | −1.2 | 1.1 | 65.1 | 44.9 |
| Prob | 0.010 | 0.010 | 0.949 | 0.597 | 0.286 | 0.010 | 0.019 | 0.004 | 0.000 | 0.000 |

| Stat | TASBLS SCORE ABS | TASSZ SCORE ABS | PLTHT CM ABS | EARHT CM ABS | STAGRN SCORE ABS | STKLDG % NOT ABS | SCTGRN SCORE ABS | EARSZ SCORE ABS | TEXEAR SCORE ABS | EARMLD SCORE ABS | BARPLT % NOT ABS |
|---|---|---|---|---|---|---|---|---|---|---|---|
| Mean1 | 9.0 | 6.3 | 235.6 | 74.4 | 6.7 | 100.0 | 7.4 | 5.4 | 7.6 | 7.2 | 95.1 |
| Mean2 | 9.0 | 5.8 | 217.3 | 81.6 | 5.8 | 100.0 | 7.5 | 4.8 | 7.5 | 7.1 | 98.0 |
| Locs | 9 | 74 | 73 | 7 | 26 | 4 | 25 | 5 | 11 | 12 | 46 |
| Reps | 9 | 74 | 73 | 7 | 26 | 4 | 25 | 5 | 11 | 12 | 47 |
| Diff | 0.0 | 0.5 | 18.3 | −7.3 | 0.9 | 0.0 | −0.2 | 0.6 | 0.1 | 0.1 | −2.9 |
| Prob | 1.000 | 0.001 | 0.000 | 0.064 | 0.013 | 1.000 | 0.557 | 0.071 | 0.676 | 0.820 | 0.021 |

| Stat | GLFSPT SCORE ABS | NLFBLT SCORE ABS | SLFBLT SCORE ABS | STWWLT SCORE ABS | ANTROT SCORE ABS | MDMCPX SCORE ABS | FUSERS SCORE ABS | GIBERS SCORE ABS | DIPERS SCORE ABS | COMRST SCORE ABS |
|---|---|---|---|---|---|---|---|---|---|---|
| Mean1 | 6.3 | 5.5 | 7.4 | 5.0 | 4.0 | 2.0 | 5.7 | 9.0 | 4.4 | 6.3 |
| Mean2 | 7.2 | 6.7 | 6.6 | 7.0 | 5.6 | 3.3 | 6.2 | 9.0 | 6.9 | 5.6 |
| Locs | 22 | 7 | 7 | 1 | 8 | 3 | 23 | 2 | 4 | 9 |
| Reps | 31 | 14 | 12 | 1 | 15 | 6 | 31 | 2 | 7 | 11 |
| Diff | −0.8 | −1.2 | 0.8 | −2.0 | −1.6 | −1.3 | −0.5 | 0.0 | −2.5 | 0.7 |
| Prob | 0.003 | 0.075 | 0.002 | | 0.089 | 0.094 | 0.065 | 1.000 | 0.123 | 0.134 |

| Stat | SOURST SCORE ABS | ECB1LF SCORE ABS | ECB2SC SCORE ABS | CLDTST PCT ABS | CLDTST PCT % MN | KSZDCD PCT ABS | HD SMT % NOT ABS | ERTLDG % NOT ABS | ERTLPN % NOT ABS |
|---|---|---|---|---|---|---|---|---|---|
| Mean1 | 2.0 | 7.0 | 4.0 | 94.5 | 102.8 | 12.3 | 98.0 | 71.6 | 96.3 |
| Mean2 | 2.0 | 9.0 | 2.0 | 87.8 | 95.5 | 7.0 | 96.4 | 61.8 | 92.7 |
| Locs | 1 | 1 | 1 | 4 | 4 | 4 | 4 | 2 | 3 |
| Reps | 1 | 2 | 2 | 4 | 4 | 4 | 8 | 2 | 3 |
| Diff | 0.0 | −2.0 | 2.0 | 6.8 | 7.3 | 5.3 | 1.6 | 9.9 | 3.7 |
| Prob | | | | 0.125 | 0.122 | 0.050 | 0.364 | 0.807 | 0.368 |

TABLE 3D

PAIRED INBRED COMPARISON REPORT
Variety #1: PH87P
Variety #2: PH8DB

| Stat | YIELD BU/A 56# ABS | YIELD BU/A 56# % MN | MST PCT ABS | EGRWTH SCORE ABS | ESTCNT COUNT ABS | TILLER PCT ABS |
|---|---|---|---|---|---|---|
| Mean1 | 179.6 | 156.0 | 24.2 | 5.7 | 22.7 | 8.2 |
| Mean2 | 136.5 | 116.1 | 21.8 | 5.8 | 23.3 | 8.5 |
| Locs | 4 | 4 | 4 | 41 | 32 | 29 |
| Reps | 8 | 8 | 8 | 41 | 45 | 29 |
| Diff | 43.1 | 39.9 | −2.4 | −0.1 | −0.6 | 0.3 |
| Prob | 0.024 | 0.055 | 0.056 | 0.309 | 0.316 | 0.912 |

| Stat | GDUSHD GDU ABS | GDUSLK GDU ABS | POLWT VALUE ABS | POLWT VALUE % MN | TASBLS SCORE ABS | TASSZ SCORE ABS |
|---|---|---|---|---|---|---|
| Mean1 | 148.9 | 153.5 | 196.6 | 129.7 | 8.0 | 6.2 |
| Mean2 | 146.1 | 147.9 | 148.0 | 95.2 | 7.6 | 5.4 |
| Locs | 99 | 100 | 17 | 17 | 8 | 82 |
| Reps | 99 | 100 | 32 | 32 | 8 | 82 |
| Diff | 2.7 | 5.6 | 48.6 | 34.5 | 0.4 | 0.8 |
| Prob | 0.000 | 0.000 | 0.003 | 0.004 | 0.869 | 0.000 |

TABLE 3D-continued

PAIRED INBRED COMPARISON REPORT
Variety #1: PH87P
Variety #2: PH8DB

| Stat | PLTHT CM ABS | EARHT CM ABS | STAGRN SCORE ABS | STKLDG % NOT ABS | SCTGRN SCORE ABS | EARSZ SCORE ABS |
|---|---|---|---|---|---|---|
| Mean1 | 235.7 | 78.2 | 6.6 | 100.0 | 7.3 | 5.4 |
| Mean2 | 224.7 | 81.0 | 4.8 | 100.0 | 7.8 | 5.2 |
| Locs | 80 | 9 | 27 | 4 | 23 | 5 |
| Reps | 80 | 9 | 27 | 4 | 23 | 5 |
| Diff | 11.0 | −2.8 | 1.8 | 0.0 | −0.6 | 0.2 |
| Prob | 0.000 | 0.389 | 0.000 | 1.000 | 0.067 | 0.621 |

| Stat | TEXEAR SCORE ABS | EARMLD SCORE ABS | BARPLT % NOT ABS | GLFSPT SCORE ABS | SLFBLT SCORE ABS | FUSERS SCORE ABS |
|---|---|---|---|---|---|---|
| Mean1 | 7.6 | 7.2 | 95.5 | 6.6 | 6.0 | 6.7 |
| Mean2 | 6.4 | 6.9 | 97.7 | 6.0 | 4.7 | 6.1 |
| Laos | 10 | 12 | 46 | 11 | 3 | 12 |
| Reps | 10 | 12 | 46 | 11 | 3 | 12 |
| Diff | 1.2 | 0.3 | −2.2 | 0.6 | 1.3 | 0.6 |
| Prob | 0.003 | 0.515 | 0.068 | 0.111 | 0.270 | 0.239 |

| Stat | GIBERS SCORE ABS | DIPERS SCORE ABS | COMRST SCORE ABS | SOURST SCORE ABS | CLDTST PCT ABS | CLDTST PCT % MN |
|---|---|---|---|---|---|---|
| Mean1 | 9.0 | 9.0 | 6.3 | 2.0 | 97.0 | 104.9 |
| Mean2 | 9.0 | 9.0 | 5.6 | 2.0 | 95.7 | 103.4 |
| Locs | 1 | 1 | 7 | 2 | 3 | 3 |
| Reps | 1 | 1 | 7 | 2 | 3 | 3 |
| Diff | 0.0 | 0.0 | 0.7 | 0.0 | 1.3 | 1.4 |
| Prob | | | 0.220 | 1.000 | 0.423 | 0.423 |

| Stat | KSZDCD PCT ABS | ERTLDG % NOT ABS | ERTLPN % NOT ABS |
|---|---|---|---|
| Mean1 | 10.0 | 71.6 | 93.0 |
| Mean2 | 22.0 | 85.8 | 99.7 |
| Laos | 3 | 2 | 3 |
| Reps | 3 | 2 | 3 |
| Diff | −12.0 | −14.2 | −6.7 |
| Prob | 0.335 | 0.141 | 0.424 |

TABLE 3E

PAIRED INBRED COMPARISON REPORT
Variety #1: PH87P
Variety #2: PH70R

| Stat | YIELD BU/A 56# ABS | YIELD BU/A 56# % MN | MST PCT ABS | TSTWT LB/BU ABS | EGRWTH SCORE ABS | ESTCNT COUNT ABS |
|---|---|---|---|---|---|---|
| Mean1 | 127.6 | 130.8 | 21.1 | 56.9 | 5.7 | 22.8 |
| Mean2 | 99.8 | 103.5 | 19.6 | 54.3 | 5.7 | 22.0 |
| Locs | 21 | 21 | 22 | 2 | 41 | 32 |
| Reps | 26 | 26 | 29 | 2 | 41 | 32 |
| Diff | 27.7 | 27.3 | −1.5 | 2.6 | 0.0 | 0.9 |
| Prob | 0.000 | 0.000 | 0.091 | 0.500 | 1.000 | 0.203 |

| Stat | TILLER PCT ABS | GDUSHD GDU ABS | GDUSLK GDU ABS | POLWT VALUE ABS | POLWT VALUE % MN | TASBLS SCORE ABS |
|---|---|---|---|---|---|---|
| Mean1 | 7.1 | 148.8 | 153.5 | 189.5 | 120.8 | 9.0 |
| Mean2 | 1.2 | 146.0 | 148.9 | 142.7 | 87.5 | 9.0 |
| Locs | 35 | 102 | 103 | 37 | 37 | 10 |
| Reps | 35 | 102 | 103 | 67 | 67 | 10 |
| Diff | −5.9 | 2.8 | 4.6 | 46.8 | 33.3 | 0.0 |
| Prob | 0.006 | 0.000 | 0.000 | 0.000 | 0.000 | 1.000 |

TABLE 3E-continued

PAIRED INBRED COMPARISON REPORT
Variety #1: PH87P
Variety #2: PH70R

| Stat | TASSZ SCORE ABS | PLTHT CM ABS | EARHT CM ABS | STAGRN SCORE ABS | STKLDG % NOT ABS | SCTGRN SCORE ABS |
|---|---|---|---|---|---|---|
| Mean1 | 6.2 | 235.2 | 78.0 | 6.5 | 99.3 | 7.4 |
| Mean2 | 4.6 | 254.0 | 82.3 | 7.1 | 99.2 | 7.0 |
| Locs |  | 83 | 10 | 28 | 8 | 25 |
| Reps | 83 | 83 | 10 | 28 | 8 | 25 |
| Diff | 1.5 | −18.9 | −4.3 | −0.6 | 0.1 | 0.3 |
| Prob | 0.000 | 0.000 | 0.295 | 0.015 | 0.744 | 0.256 |

| Stat | EARSZ SCORE ABS | TEXEAR SCORE ABS | EARMLD SCORE ABS | BARPLT % NOT ABS | DRPEAR % NOT ABS | GLFSPT SCORE ABS |
|---|---|---|---|---|---|---|
| Mean1 | 5.4 | 7.6 | 7.2 | 95.3 | 100.0 | 6.3 |
| Mean2 | 4.4 | 7.4 | 5.1 | 94.8 | 100.0 | 6.4 |
| Locs | 5 | 11 | 12 | 52 | 4 | 24 |
| Reps | 5 | 11 | 12 | 53 | 4 | 32 |
| Diff | 1.0 | 0.3 | 2.1 | 0.4 | 0.0 | −0.1 |
| Prob | 0.189 | 0.341 | 0.001 | 0.672 | 1.000 | 0.518 |

| Stat | NLFBLT SCORE ABS | SLFBLT SCORE ABS | STWWLT SCORE ABS | ANTROT SCORE ABS | MDMCPX SCORE ABS | FUSERS SCORE ABS |
|---|---|---|---|---|---|---|
| Mean1 | 5.5 | 7.1 | 5.0 | 4.0 | 2.0 | 5.6 |
| Mean2 | 5.0 | 5.8 | 7.0 | 5.3 | 3.0 | 4.1 |
| Locs | 7 | 9 | 1 | 8 | 3 | 25 |
| Reps | 14 | 14 | 1 | 15 | 6 | 33 |
| Diff | 0.5 | 1.2 | −2.0 | −1.3 | −1.0 | 1.5 |
| Prob | 0.156 | 0.017 |  | 0.049 | 0.074 | 0.000 |

| Stat | GIBERS SCORE ABS | DIPERS SCORE ABS | COMRST SCORE ABS | SOURST SCORE ABS | ECB1LF SCORE ABS | ECB2SC SCORE ABS |
|---|---|---|---|---|---|---|
| Mean1 | 9.0 | 4.4 | 6.3 | 2.0 | 7.0 | 4.0 |
| Mean2 | 9.0 | 3.8 | 4.5 | 2.0 | 6.0 | 3.0 |
| Locs | 2 | 4 | 9 | 2 | 1 | 1 |
| Reps | 2 | 7 | 11 | 2 | 2 | 2 |
| Diff | 0.0 | 0.6 | 1.8 | 0.0 | 1.0 | 1.0 |
| Prob | 1.000 | 0.516 | 0.001 | 1.000 |  |  |

| Stat | CLDTST PCT ABS | CLDTST PCT % MN | KSZDCD PCT ABS | HD SMT % NOT ABS | ERTLDG % NOT ABS | LRTLDG % NOT ABS | ERTLPN % NOT ABS |
|---|---|---|---|---|---|---|---|
| Mean1 | 87.3 | 98.9 | 7.2 | 98.0 | 71.6 | 96.2 | 93.8 |
| Mean2 | 82.6 | 93.9 | 2.2 | 97.8 | 27.3 | 99.2 | 95.8 |
| Locs | 9 | 9 | 9 | 4 | 2 | 2 | 5 |
| Reps | 9 | 9 | 9 | 8 | 2 | 2 | 5 |
| Diff | 4.8 | 5.0 | 5.0 | 0.1 | 44.4 | −2.9 | −2.0 |
| Prob | 0.209 | 0.266 | 0.028 | 0.941 | 0.222 | 0.641 | 0.379 |

TABLE 3F

PAIRED INBRED COMPARISON REPORT
Variety #1: PH87P
Variety #2: PH6B8

| Stat | EGRWTH SCORE ABS | ESTCNT COUNT ABS | TILLER PCT ABS | GDUSHD GDU ABS | GDUSLK GDU ABS | TASBLS SCORE ABS |
|---|---|---|---|---|---|---|
| Mean1 | 5.8 | 19.5 | 14.0 | 143.7 | 147.5 | 9.0 |
| Mean2 | 5.7 | 19.2 | 2.4 | 149.4 | 150.2 | 9.0 |
| Locs | 24 | 17 | 15 | 33 | 33 | 6 |
| Reps | 24 | 17 | 15 | 33 | 33 | 6 |
| Diff | 0.1 | 0.2 | −11.6 | −5.7 | −2.7 | 0.0 |
| Prob | 0.328 | 0.705 | 0.013 | 0.000 | 0.003 | 1.000 |

TABLE 3F-continued

PAIRED INBRED COMPARISON REPORT
Variety #1: PH87P
Variety #2: PH6B8

| Stat | TASSZ SCORE ABS | PLTHT CM ABS | EARHT CM ABS | STAGRN SCORE ABS | STKLDG % NOT ABS | SCTGRN SCORE ABS |
|---|---|---|---|---|---|---|
| Mean1 | 6.0 | 239.3 | 84.7 | 5.0 | 100.0 | 7.4 |
| Mean2 | 5.8 | 231.7 | 84.7 | 5.8 | 96.3 | 7.3 |
| Locs | 27 | 29 | 3 | 5 | 3 | 7 |
| Reps | 27 | 29 | 3 | 5 | 3 | 7 |
| Diff | 0.2 | 7.6 | 0.0 | −0.8 | 3.7 | 0.1 |
| Prob | 0.185 | 0.021 | 1.000 | 0.242 | 0.184 | 0.818 |

| Stat | EARSZ SCORE ABS | TEXEAR SCORE ABS | EARMLD SCORE ABS | BARPLT % NOT ABS | GLFSPT SCORE ABS | NLFBLT SCORE ABS |
|---|---|---|---|---|---|---|
| Mean1 | 5.0 | 7.0 | 7.4 | 99.2 | 5.5 | 6.0 |
| Mean2 | 6.0 | 6.0 | 7.9 | 99.7 | 4.8 | 5.0 |
| Locs | 1 | 1 | 7 | 17 | 6 | 1 |
| Reps | 1 | 1 | 7 | 17 | 7 | 2 |
| Diff | −1.0 | 1.0 | −0.4 | −0.5 | 0.7 | 1.0 |
| Prob |  |  | 0.356 | 0.421 | 0.175 |  |

| Stat | SLFBLT SCORE ABS | ANTROT SCORE ABS | FUSERS SCORE ABS | COMRST SCORE ABS | SOURST SCORE ABS | ERTLPN % NOT ABS |
|---|---|---|---|---|---|---|
| Mean1 | 6.2 | 4.0 | 6.6 | 5.5 | 2.0 | 80.0 |
| Mean2 | 5.3 | 3.3 | 7.1 | 7.0 | 2.0 | 80.0 |
| Locs | 3 | 2 | 11 | 2 | 1 | 1 |
| Reps | 4 | 3 | 12 | 2 | 1 | 1 |
| Diff | 0.8 | 0.8 | −0.5 | −1.5 | 0.0 | 0.0 |
| Prob | 0.038 | 0.205 | 0.052 | 0.205 |  |  |

TABLE 4A

Average Inbred By Tester Performance Comparing PH87P To PH1BC Crossed To The Same Inbred Testers And Grown In The Same Experiments.

|  | YIELD BU/A 56# | MST PCT | EGRWTH SCORE | ESTCNT COUNT | GDUSHD GDU | GDUSLK GDU |
|---|---|---|---|---|---|---|
| Reps | 293 | 299 | 28 | 15 | 69 | 47 |
| Locs | 293 | 299 | 28 | 15 | 69 | 47 |
| PH87P | 195.1 | 21.8 | 6.1 | 54.7 | 141.4 | 142.7 |
| PH1BC | 190.8 | 22.2 | 6.1 | 52.5 | 141.4 | 142.7 |
| Diff | 4.3 | 0.4 | 0.1 | 2.2 | 0.0 | 0.0 |
| Pr > T | 0.003 | 0.000 | 0.800 | 0.016 | 0.944 | 0.987 |

|  | PLTHT CM | EARHT CM | STAGRN SCORE | TSTWT LB/BU ABS | GLFSPT SCORE ABS | NLFBLT SCORE ABS |
|---|---|---|---|---|---|---|
| Reps | 69 | 69 | 68 | 217 | 27 | 8 |
| Locs | 69 | 69 | 68 | 217 | 27 | 8 |
| PH87P | 317.8 | 131.3 | 4.8 | 57.4 | 6.0 | 4.8 |
| PH1BC |  | 137.5 | 5.5 | 57.3 | 5.5 | 5.1 |
| Diff | 6.8 | 6.1 | 0.6 | 0.1 | 0.5 | 0.4 |
| Pr > T | 0.000 | 0.000 | 0.000 | 0.629 | 0.015 | 0.285 |

|  | SLFBLT SCORE ABS | ANTROT SCORE ABS | FUSERS SCORE ABS | DIPERS SCORE ABS | COMRST SCORE ABS | ECB1LF SCORE ABS |
|---|---|---|---|---|---|---|
| Reps | 8 | 21 | 14 | 4 | 1 | 1 |
| Locs | 8 | 21 | 14 | 4 | 1 | 1 |
| PH87P | 6.4 | 4.6 | 6.3 | 3.6 | 6.0 | 1.0 |
| PH1BC | 5.2 | 3.9 | 4.7 | 3.0 | 4.0 | 3.5 |
| Diff | 1.3 | 0.7 | 1.5 | 0.6 | 2.0 | 2.5 |
| Pr > T | 0.052 | 0.082 | 0.000 | 0.412 |  |  |

TABLE 4A-continued

Average Inbred By Tester Performance Comparing PH87P To PH1BC Crossed
To The Same Inbred Testers And Grown In The Same Experiments.

|  | ECB2SC SCORE ABS | GIBROT SCORE ABS | BRTSTK % NOT ABS | STLLPN % NOT ABS | EBTSTK % NOT ABS | ABTSTK % NOT ABS |
|---|---|---|---|---|---|---|
| Reps | 5 | 26 | 2 | 4 | 55 | 1 |
| Locs | 5 | 26 | 2 | 4 | 55 | 1 |
| PH87P | 4.3 | 5.0 | 4.5 | 97.4 | 70.4 | 3.0 |
| PH1BC | 3.0 | 5.4 | 1.8 | 98.2 | 62.4 | 4.5 |
| Diff | 1.3 | 0.3 | 2.8 | 0.9 | 8.1 | 1.5 |
| Pr > T | 0.012 | 0.171 | 0.361 | 0.523 | 0.004 |  |

*Pr > T values are valid only for comparisons with Locs >= 10

TABLE 4B

Average Inbred By Tester Performance Comparing PH87P To PH21T Crossed
To The Same Inbred Testers And Grown In The Same Experiments.

|  | YIELD BU/A 56# | MST PCT | EGRWTH SCORE | GDUSHD GDU | GDUSLK GDU | PLTHT CM | EARHT CM | STAGRN SCORE | TSTWT LB/BU ABS |
|---|---|---|---|---|---|---|---|---|---|
| Reps | 117 | 117 | 10 | 29 | 16 | 28 | 28 | 30 | 88 |
| Locs | 117 | 117 | 10 | 29 | 16 | 28 | 28 | 30 | 88 |
| PH87P | 189.6 | 21.4 | 5.9 | 139.2 | 142.6 | 326.7 | 139.8 | 4.3 | 57.3 |
| PH21T | 193.8 | 22.0 | 5.4 | 138.3 | 138.6 | 317.1 | 141.5 | 5.2 | 56.9 |
| Diff | 4.2 | 0.6 | 0.5 | 0.9 | 4.1 | 9.6 | 1.7 | 0.9 | 0.3 |
| Pr > T | 0.070 | 0.003 | 0.138 | 0.200 | 0.054 | 0.001 | 0.486 | 0.000 | 0.057 |

|  | GLFSPT SCORE ABS | NLFBLT SCORE ABS | SLFBLT SCORE ABS | ANTROT SCORE ABS | FUSERS SCORE ABS | DIPERS SCORE ABS | GIBROT SCORE ABS | STLLPN % NOT ABS | EBTSTK % NOT ABS |
|---|---|---|---|---|---|---|---|---|---|
| Reps | 12 | 1 | 3 | 5 | 4 | 1 | 14 | 2 | 26 |
| Locs | 12 | 1 | 3 | 5 | 4 | 1 | 14 | 2 | 26 |
| PH87P | 5.5 | 5.0 | 6.5 | 4.4 | 6.4 | 3.5 | 4.3 | 96.1 | 54.8 |
| PH21T | 6.0 | 6.0 | 6.7 | 5.3 | 4.6 | 3.0 | 6.4 | 100.0 | 65.8 |
| Diff | 0.5 | 1.0 | 0.2 | 0.9 | 1.8 | 0.5 | 2.1 | 3.9 | 11.0 |
| Pr > T | 0.237 |  | 0.423 | 0.338 | 0.110 |  | 0.003 | 0.500 | 0.036 |

*Pr > T values are valid only for comparisons with Locs >= 10

TABLE 4C

Average Inbred By Tester Performance Comparing
PH87P To PH70R Crossed To The Same Inbred Testers
And Grown In The Same Experiments.

|  | YIELD BU/A 56# | MST PCT | EGRWTH SCORE | ESTCNT COUNT | GDUSHD GDU |
|---|---|---|---|---|---|
| Reps | 760 | 771 | 54 | 55 | 211 |
| Locs | 760 | 771 | 54 | 55 | 211 |
| PH87P | 189.2 | 21.7 | 5.8 | 53.7 | 142.0 |
| PH70R | 190.7 | 21.9 | 5.9 | 53.5 | 142.0 |
| Diff | 1.5 | 0.1 | 0.1 | 0.2 | 0.1 |
| Pr > T | 0.079 | 0.017 | 0.549 | 0.672 | 0.808 |

|  | GDUSLK GDU | PLTHT CM | EARHT CM | STAGRN SCORE | TSTWT LB/BU ABS |
|---|---|---|---|---|---|
| Reps | 167 | 242 | 229 | 215 | 573 |
| Locs | 167 | 242 | 229 | 215 | 573 |
| PH87P | 142.6 | 315.4 | 130.1 | 4.8 | 57.4 |
| PH70R | 142.6 | 325.9 | 138.3 | 5.4 | 57.2 |
| Diff | 0.0 | 10.5 | 8.2 | 0.6 | 0.2 |
| Pr > T | 0.979 | 0.000 | 0.000 | 0.000 | 0.027 |

TABLE 4C-continued

Average Inbred By Tester Performance Comparing
PH87P To PH70R Crossed To The Same Inbred Testers
And Grown In The Same Experiments.

|  | GLFSPT SCORE ABS | NLFBLT SCORE ABS | SLFBLT SCORE ABS | ANTROT SCORE ABS | FUSERS SCORE ABS |
|---|---|---|---|---|---|
| Reps | 66 | 19 | 20 | 41 | 29 |
| Locs | 66 | 19 | 20 | 41 | 29 |
| PH87P | 6.0 | 5.3 | 6.6 | 4.2 | 5.9 |
| PH70R | 5.7 | 4.9 | 5.5 | 4.9 | 5.2 |
| Diff | 0.3 | 0.4 | 1.2 | 0.7 | 0.7 |
| Pr > T | 0.012 | 0.012 | 0.000 | 0.000 | 0.001 |

|  | GIBERS SCORE ABS | DIPERS SCORE ABS | COMRST SCORE ABS | ECB1LF SCORE ABS | ECB2SC SCORE ABS |
|---|---|---|---|---|---|
| Reps | 1 | 10 | 1 | 4 | 10 |
| Locs | 1 | 10 | 1 | 4 | 10 |
| PH87P | 8.0 | 3.1 | 6.0 | 3.0 | 4.0 |
| PH70R | 9.0 | 3.9 | 4.0 | 3.5 | 3.4 |
| Diff | 1.0 | 0.9 | 2.0 | 0.5 | 0.6 |
| Pr > T |  | 0.067 |  | 0.252 | 0.041 |

TABLE 4C-continued

Average Inbred By Tester Performance Comparing PH87P To PH70R Crossed To The Same Inbred Testers And Grown In The Same Experiments.

|  | GIBROT SCORE | BRTSTK % NOT ABS | STLLPN % NOT ABS | EBTSTK % NOT ABS | ABTSTK % NOT ABS |
|---|---|---|---|---|---|
| Reps | 65 | 9 | 6 | 189 | 4 |
| Locs | 65 | 9 | 6 | 189 | 4 |
| PH87P | 5.4 | 4.6 | 97.1 | 70.1 | 3.5 |
| PH70R | 6.4 | 4.9 | 96.4 | 76.9 | 3.9 |
| Diff | 1.0 | 0.4 | 0.6 | 6.8 | 0.4 |
| Pr > T | 0.000 | 0.594 | 0.701 | 0.000 | 0.718 |

*Pr > T values are valid only for comparisons with Locs >= 10

TABLE 5

General Combining Ability Report for Inbred PH87P

| YIELD bu/a 56# ABS | Mean | 183.5 |
|---|---|---|
| YIELD bu/a 56# ABS | Locs | 349 |
| YIELD bu/a 56# ABS | Reps | 3901 |
| YIELD bu/a 56# ABS | Years | 4 |
| MST pct ABS | Mean | 21.5 |
| MST pct ABS | Locs | 351 |
| MST pct ABS | Reps | 3946 |
| MST pct ABS | Years | 4 |
| EGRWTH score ABS | Mean | 5.8 |
| EGRWTH score ABS | Locs | 29 |
| EGRWTH score ABS | Reps | 296 |
| EGRWTH score ABS | Years | 4 |
| ESTCNT count ABS | Mean | 56.2 |
| ESTCNT count ABS | Locs | 27 |

TABLE 4D

Average Inbred By Tester Performance Comparing PH87P To PH8DB Crossed To The Same Inbred Testers And Grown In The Same Experiments.

|  | YIELD BU/A 56# | MST PCT | EGRWTH SCORE | ESTCNT COUNT | GDUSHD GDU | GDUSLK GDU |
|---|---|---|---|---|---|---|
| Reps | 680 | 685 | 39 | 1 | 188 | 72 |
| Locs | 680 | 685 | 39 | 1 | 188 | 72 |
| PH87P | 189.2 | 22.1 | 6.0 | 60.0 | 142.1 | 143.9 |
| PH8DB | 186.9 | 21.7 | 6.2 | 58.0 | 140.7 | 141.9 |
| Diff | 2.3 | 0.4 | 0.2 | 2.0 | 1.3 | 2.0 |
| Pr > T | 0.014 | 0.000 | 0.399 |  | 0.000 | 0.000 |

|  | PLTHT CM | EARHT CM | STAGRN SCORE | TSTWT LB/BU ABS | GLFSPT SCORE ABS | NLFBLT SCORE ABS |
|---|---|---|---|---|---|---|
| Reps | 189 | 189 | 211 | 505 | 44 | 3 |
| Locs | 189 | 189 | 211 | 505 | 44 | 3 |
| PH87P | 316.3 | 132.2 | 4.9 | 57.2 | 6.0 | 5.3 |
| PH8DB | 315.3 | 131.2 | 4.5 | 56.6 | 5.3 | 4.8 |
| Diff | 1.0 | 1.0 | 0.4 | 0.5 | 0.7 | 0.5 |
| Pr > T | 0.353 | 0.239 | 0.001 | 0.000 | 0.000 | 0.580 |

|  | SLFBLT SCORE ABS | ANTROT SCORE ABS | FUSERS SCORE ABS | GIBERS SCORE ABS | DIPERS SCORE ABS | GIBROT SCORE ABS |
|---|---|---|---|---|---|---|
| Reps | 6 | 7 | 4 | 2 | 2 | 74 |
| Locs | 6 | 7 | 4 | 2 | 2 | 74 |
| PH87P | 6.6 | 3.9 | 5.5 | 7.0 | 5.3 | 6.0 |
| PH8DB | 5.9 | 4.3 | 3.6 | 7.0 | 3.0 | 5.7 |
| Diff | 0.7 | 0.4 | 1.9 | 0.0 | 2.3 | 0.2 |
| Pr > T | 0.025 | 0.457 | 0.009 | 1.000 | 0.205 | 0.292 |

|  | BRTSTK % NOT ABS | STLLPN % NOT ABS | EBTSTK % NOT ABS |
|---|---|---|---|
| Reps | 1 | 1 | 196 |
| Locs | 1 | 1 | 196 |
| PH87P | 1.0 | 99.1 | 64.3 |
| PH8DB | 3.0 | 100.0 | 60.8 |
| Diff | 2.0 | 0.9 | 3.5 |
| Pr > T |  |  | 0.027 |

*Pr > T values are valid only for comparisons with Locs >= 10

TABLE 5-continued

General Combining Ability Report for Inbred PH87P

| | | |
|---|---|---|
| ESTCNT count ABS | Reps | 589 |
| ESTCNT count ABS | Years | 3 |
| GDUSHD GDU ABS | Mean | 143.3 |
| GDUSHD GDU ABS | Locs | 82 |
| GDUSHD GDU ABS | Reps | 1077 |
| GDUSHD GDU ABS | Years | 4 |
| GDUSLK GDU ABS | Mean | 145.1 |
| GDUSLK GDU ABS | Locs | 78 |
| GDUSLK GDU ABS | Reps | 668 |
| GDUSLK GDU ABS | Years | 4 |
| PLTHT cm ABS | Mean | 309.8 |
| PLTHT cm ABS | Locs | 103 |
| PLTHT cm ABS | Reps | 1229 |
| PLTHT cm ABS | Years | 4 |
| EARHT cm ABS | Mean | 126.1 |
| EARHT cm ABS | Locs | 92 |
| EARHT cm ABS | Reps | 1199 |
| EARHT cm ABS | Years | 4 |
| STAGRN score ABS | Mean | 4.6 |
| STAGRN score ABS | Locs | 105 |
| STAGRN score ABS | Reps | 1295 |
| STAGRN score ABS | Years | 4 |
| TSTWT lb/bu ABS | Mean | 57.3 |
| TSTWT lb/bu ABS | Locs | 305 |
| TSTWT lb/bu ABS | Reps | 3461 |
| TSTWT lb/bu ABS | Years | 4 |
| GLFSPT score ABS | Mean | 5.9 |
| GLFSPT score ABS | Locs | 32 |
| GLFSPT score ABS | Reps | 336 |
| GLFSPT score ABS | Years | 4 |
| NLFBLT score ABS | Mean | 4.9 |
| NLFBLT score ABS | Locs | 8 |
| NLFBLT score ABS | Reps | 68 |
| NLFBLT score ABS | Years | 3 |
| SLFBLT score ABS | Mean | 6.5 |
| SLFBLT score ABS | Locs | 5 |
| SLFBLT score ABS | Reps | 62 |
| SLFBLT score ABS | Years | 3 |
| ANTROT score ABS | Mean | 4.2 |
| ANTROT score ABS | Locs | 18 |
| ANTROT score ABS | Reps | 140 |
| ANTROT score ABS | Years | 3 |
| FUSERS score ABS | Mean | 6.1 |
| FUSERS score ABS | Locs | 8 |
| FUSERS score ABS | Reps | 72 |
| FUSERS score ABS | Years | 3 |
| DIPERS score ABS | Mean | 3.6 |
| DIPERS score ABS | Locs | 5 |
| DIPERS score ABS | Reps | 46 |
| DIPERS score ABS | Years | 3 |
| COMRST score ABS | Mean | 6 |
| COMRST score ABS | Locs | 1 |
| COMRST score ABS | Reps | 1 |
| COMRST score ABS | Years | 1 |
| SOURST score ABS | Mean | 2.6 |
| SOURST score ABS | Locs | 1 |
| SOURST score ABS | Reps | 74 |
| SOURST score ABS | Years | 1 |
| ECB1LF score ABS | Mean | 4.2 |
| ECB1LF score ABS | Locs | 5 |
| ECB1LF score ABS | Reps | 45 |
| ECB1LF score ABS | Years | 2 |
| ECB2SC score ABS | Mean | 6 |
| ECB2SC score ABS | Locs | 18 |
| ECB2SC score ABS | Reps | 234 |
| ECB2SC score ABS | Years | 3 |
| GIBROT score ABS | Mean | 4.5 |
| GIBROT score ABS | Locs | 5 |
| GIBROT score ABS | Reps | 58 |
| GIBROT score ABS | Years | 1 |
| BRTSTK % NOT ABS | Mean | 98.8 |
| BRTSTK % NOT ABS | Locs | 3 |
| BRTSTK % NOT ABS | Reps | 23 |
| BRTSTK % NOT ABS | Years | 2 |
| STLLPN % NOT ABS | Mean | 73.8 |
| STLLPN % NOT ABS | Locs | 58 |
| STLLPN % NOT ABS | Reps | 1216 |
| STLLPN % NOT ABS | Years | 4 |
| DIPROT score ABS | Mean | 4 |
| DIPROT score ABS | Locs | 1 |
| DIPROT score ABS | Reps | 20 |
| DIPROT score ABS | Years | 1 |
| EBTSTK % NOT ABS | Mean | 95.3 |
| EBTSTK % NOT ABS | Locs | 2 |
| EBTSTK % NOT ABS | Reps | 3 |
| EBTSTK % NOT ABS | Years | 1 |
| ABTSTK % NOT ABS | Mean | 63.4 |
| ABTSTK % NOT ABS | Locs | 17 |
| ABTSTK % NOT ABS | Reps | 215 |
| ABTSTK % NOT ABS | Years | 4 |
| ERTLPN % NOT ABS | Mean | 76.6 |
| ERTLPN % NOT ABS | Locs | 24 |
| ERTLPN % NOT ABS | Reps | 379 |
| ERTLPN % NOT ABS | Years | 2 |
| LRTLPN % NOT ABS | Mean | 69.8 |
| LRTLPN % NOT ABS | Locs | 40 |
| LRTLPN % NOT ABS | Reps | 435 |
| LRTLPN % NOT ABS | Years | 2 |
| DIPERS score ABS | Years | 3 |

TABLE 5A

Combining Ability Report for Inbred PH87P
F1 data for Inbred Line PH87P when crossed to various tester lines

| Tester | YIELD bu/a 56# ABS Mean | YIELD bu/a 56# ABS Locs | YIELD bu/a 56# ABS Reps | MST pct ABS Mean | MST pct ABS Locs | MST pct ABS Reps |
|---|---|---|---|---|---|---|
| 75231B | 175.3 | 16 | 19 | 21.6 | 16 | 19 |
| 75229A | 187.2 | 16 | 19 | 23 | 16 | 19 |
| 53300D | 154.5 | 35 | 39 | 22 | 35 | 39 |
| 56798D | 201.8 | 18 | 18 | 21.9 | 18 | 18 |
| 56807G | 199.8 | 32 | 32 | 20.6 | 33 | 33 |
| 57072E | 176.4 | 17 | 17 | 22.3 | 17 | 17 |
| 61682H | 170.6 | 17 | 17 | 20.3 | 17 | 17 |
| 75226A | 183.6 | 17 | 17 | 21.6 | 17 | 17 |
| 752263D | 146.7 | 14 | 14 | 20.6 | 14 | 14 |
| 209391B | 160.6 | 17 | 17 | 21.9 | 17 | 17 |
| 209391D | 147.5 | 17 | 17 | 23.5 | 17 | 17 |
| 209391E | 167.9 | 17 | 17 | 20.5 | 17 | 17 |

TABLE 5A-continued

Combining Ability Report for Inbred PH87P
F1 data for Inbred Line PH87P when crossed to various tester lines

| | | | | | | |
|---|---|---|---|---|---|---|
| 212022H | 173.5 | 18 | 18 | 22.2 | 18 | 18 |
| 212023F | 158.6 | 18 | 18 | 21.8 | 18 | 18 |
| 212027B | 170.6 | 18 | 18 | 20.2 | 18 | 18 |
| 212910H | 181.9 | 16 | 19 | 21.2 | 16 | 19 |
| 51443B | 182.7 | 17 | 17 | 22.4 | 17 | 17 |
| 56800J | 206.6 | 18 | 18 | 23.4 | 18 | 18 |
| 304474J | 195.4 | 16 | 37 | 22.9 | 16 | 37 |
| 304475B | 192.4 | 16 | 37 | 22.4 | 16 | 37 |
| 304476E | 191.3 | 16 | 37 | 22.7 | 16 | 37 |

| Tester | EGRWTH score ABS Mean | EGRWTH score ABS Locs | EGRWTH score ABS Reps | ESTCNT count ABS Mean | ESTCNT count ABS Locs | ESTCNT count ABS Reps |
|---|---|---|---|---|---|---|
| 75231B | | | | | | |
| 75229A | | | | | | |
| 53300D | 5.7 | 3 | 3 | 60 | 1 | 1 |
| 56798D | 8 | 1 | 1 | | | |
| 56807G | 6.7 | 7 | 7 | | | |
| 57072E | | | | | | |
| 61682H | 8 | 1 | 1 | | | |
| 75226A | 8 | 1 | 1 | | | |
| 752263D | 5.3 | 3 | 3 | | | |
| 209391B | 5 | 3 | 3 | 60 | 1 | 1 |
| 209391D | 5.7 | 3 | 3 | 60 | 1 | 1 |
| 209391E | 5 | 3 | 3 | 59 | 1 | 1 |
| 212022H | | | | | | |
| 212023F | | | | | | |
| 212027B | | | | | | |
| 212910H | | | | | | |
| 51443B | 8 | 1 | 1 | | | |
| 56800J | 6 | 1 | 1 | | | |
| 304474J | | | | 66.2 | 4 | 14 |
| 304475B | | | | 68.4 | 4 | 14 |
| 304476E | | | | 66.6 | 4 | 14 |

| Tester | GDUSHD GDU ABS Mean | GDUSHD GDU ABS Locs | GDUSHD GDU ABS Reps | GDUSLK GDU ABS Mean | GDUSLK GDU ABS Locs | GDUSLK GDU ABS Reps |
|---|---|---|---|---|---|---|
| 75231B | 140 | 3 | 3 | 142 | 1 | 1 |
| 75229A | 144.3 | 3 | 3 | 144 | 1 | 1 |
| 53300D | 141 | 9 | 11 | 140.5 | 3 | 4 |
| 56798D | 140.3 | 4 | 4 | 128 | 1 | 1 |
| 56807G | 140.4 | 9 | 9 | 131.5 | 2 | 2 |
| 57072E | 143.4 | 5 | 5 | 139.5 | 2 | 2 |
| 61682H | 144.2 | 6 | 6 | 148.7 | 3 | 3 |
| 75226A | 141.9 | 7 | 7 | 141.5 | 2 | 2 |
| 752263D | 143.3 | 5 | 5 | | | |
| 209391B | 143.3 | 6 | 7 | 144.5 | 2 | 2 |
| 209391D | 144.3 | 6 | 7 | 144.5 | 2 | 2 |
| 209391E | 140.4 | 6 | 7 | 139.5 | 2 | 2 |
| 212022H | 145.3 | 5 | 5 | 149.4 | 4 | 4 |
| 212023F | 145 | 5 | 5 | 149.7 | 4 | 4 |
| 212027B | 144.2 | 5 | 5 | 149.4 | 4 | 4 |
| 212910H | 144.8 | 5 | 5 | 143 | 3 | 3 |
| 51443B | 141.8 | 4 | 4 | 136 | 1 | 1 |
| 56800J | 141 | 4 | 4 | 136 | 1 | 1 |
| 304474J | 148 | 9 | 25 | 150.9 | 8 | 21 |
| 304475B | 147.6 | 9 | 25 | 149.9 | 8 | 21 |
| 304476E | 148.3 | 9 | 25 | 151.6 | 8 | 21 |

| Tester | PLTHT cm ABS Mean | PLTHT cm ABS Locs | PLTHT cm ABS Reps | EARHT cm ABS Mean | EARHT cm ABS Locs | EARHT cm ABS Reps |
|---|---|---|---|---|---|---|
| 75231B | 303.3 | 5 | 5 | 111.8 | 5 | 5 |
| 75229A | 318.5 | 5 | 5 | 121.4 | 5 | 5 |
| 53300D | 279.1 | 7 | 8 | 105.1 | 7 | 8 |
| 56798D | 326.4 | 4 | 4 | 132.7 | 4 | 4 |
| 56807G | 320 | 9 | 9 | 138.3 | 9 | 9 |
| 57072E | 303.3 | 5 | 5 | 120.4 | 5 | 5 |
| 61682H | 316 | 5 | 5 | 131.1 | 5 | 5 |
| 75226A | 310.2 | 7 | 7 | 138.6 | 7 | 7 |
| 752263D | 290.2 | 4 | 4 | 117.5 | 4 | 4 |
| 209391B | 294 | 4 | 4 | 127 | 4 | 4 |

TABLE 5A-continued

Combining Ability Report for Inbred PH87P
F1 data for Inbred Line PH87P when crossed to various tester lines

| | | | | | | |
|---|---|---|---|---|---|---|
| 209391D | 271.8 | 4 | 4 | 113 | 4 | 4 |
| 209391E | 285.8 | 4 | 4 | 109.9 | 4 | 4 |
| 212022H | 327.7 | 3 | 3 | 121.9 | 3 | 3 |
| 212023F | 327.7 | 3 | 3 | 131.2 | 3 | 3 |
| 212027B | 322.6 | 3 | 3 | 129.5 | 3 | 3 |
| 212910H | 311.4 | 5 | 5 | 118.4 | 5 | 5 |
| 51443B | 334.6 | 4 | 4 | 137.8 | 4 | 4 |
| 56800J | 320.7 | 4 | 4 | 137.8 | 4 | 4 |
| 304474J | 269.5 | 6 | 20 | 109 | 6 | 20 |
| 304475B | 278.5 | 6 | 20 | 109.6 | 6 | 20 |
| 304476E | 273.8 | 6 | 20 | 109.5 | 6 | 20 |

| Tester | STAGRN score ABS Mean | STAGRN score ABS Locs | STAGRN score ABS Reps | TSTWT lb/bu ABS Mean | TSTWT lb/bu ABS Locs | TSTWT lb/bu ABS Reps |
|---|---|---|---|---|---|---|
| 75231B | 5.5 | 2 | 2 | 56.7 | 15 | 17 |
| 75229A | 5 | 2 | 2 | 57.2 | 16 | 19 |
| 53300D | 4.8 | 12 | 12 | 58.4 | 30 | 34 |
| 56798D | 4.6 | 7 | 7 | 57.4 | 15 | 15 |
| 56807G | 4.4 | 14 | 14 | 57.1 | 29 | 29 |
| 57072E | 5 | 2 | 2 | 56.5 | 15 | 15 |
| 61682H | 2.7 | 3 | 3 | 56.9 | 15 | 15 |
| 75226A | 6 | 8 | 8 | 58.9 | 12 | 12 |
| 752263D | 3.3 | 6 | 6 | 58.1 | 12 | 12 |
| 209391B | 3.8 | 10 | 10 | 57.9 | 14 | 14 |
| 209391D | 4.6 | 10 | 10 | 56.5 | 14 | 14 |
| 209391E | 3.2 | 10 | 10 | 58.2 | 14 | 14 |
| 212022H | 4.7 | 3 | 3 | 57.1 | 16 | 16 |
| 212023F | 5.3 | 3 | 3 | 57 | 16 | 16 |
| 212027B | 2.7 | 3 | 3 | 57.5 | 16 | 16 |
| 212910H | 4.8 | 4 | 4 | 57.3 | 16 | 19 |
| 51443B | 3.7 | 6 | 6 | 57.2 | 14 | 14 |
| 56800J | 5.1 | 7 | 7 | 57.4 | 15 | 15 |
| 304474J | 4.6 | 7 | 17 | 56.9 | 14 | 31 |
| 304475B | 4.2 | 7 | 17 | 57.2 | 14 | 32 |
| 304476E | 4.8 | 7 | 17 | 57 | 14 | 32 |

| Tester | GLFSPT score ABS Mean | GLFSPT score ABS Locs | GLFSPT score ABS Reps | ECB2SC score ABS Mean | ECB2SC score ABS Locs | ECB2SC score ABS Reps |
|---|---|---|---|---|---|---|
| 75231B | 6 | 1 | 1 | | | |
| 75229A | 4 | 1 | 1 | | | |
| 53300D | 5 | 2 | 2 | 6 | 1 | 1 |
| 56798D | 6 | 2 | 2 | | | |
| 56807G | 6 | 3 | 3 | | | |
| 57072E | | | | | | |
| 61682H | | | | 6 | 2 | 2 |
| 75226A | 4 | 1 | 1 | 8.3 | 3 | 3 |
| 752263D | 5.5 | 2 | 2 | 7 | 1 | 1 |
| 209391B | 4 | 2 | 2 | 2 | 1 | 1 |
| 209391D | 5.5 | 2 | 2 | 8 | 1 | 1 |
| 209391E | 5 | 2 | 2 | 4 | 1 | 1 |
| 212022H | 5 | 2 | 2 | 9 | 1 | 1 |
| 212023F | 5.5 | 2 | 2 | 9 | 1 | 1 |
| 212027B | 4.5 | 2 | 2 | 9 | 1 | 1 |
| 212910H | | | | | | |
| 51443B | 6 | 2 | 2 | | | |
| 56800J | 5.5 | 2 | 2 | | | |
| 304474J | 6.8 | 2 | 4 | 8 | 1 | 2 |
| 304475B | 6.3 | 2 | 4 | 9 | 1 | 2 |
| 304476E | 6 | 2 | 4 | 9 | 1 | 2 |

| Tester | GIBROT score ABS Mean | GIBROT score ABS Locs | GIBROT score ABS Reps | STLLPN % NOT ABS Mean | STLLPN % NOT ABS Locs | STLLPN % NOT ABS Reps |
|---|---|---|---|---|---|---|
| 75231B | | | | 84.3 | 5 | 5 |
| 75229A | | | | 57.1 | 5 | 5 |
| 53300D | 2 | 1 | 1 | 78.7 | 11 | 19 |
| 56798D | | | | 63.8 | 5 | 5 |
| 56807G | | | | 68.9 | 8 | 8 |
| 57072E | | | | 83.5 | 4 | 4 |
| 61682H | | | | 25.1 | 6 | 6 |

TABLE 5A-continued

Combining Ability Report for Inbred PH87P
F1 data for Inbred Line PH87P when crossed to various tester lines

| | | | | | | |
|---|---|---|---|---|---|---|
| 75226A | | | | 65.8 | 7 | 7 |
| 752263D | 9 | 1 | 1 | 92.6 | 4 | 5 |
| 209391B | 1 | 1 | 1 | 70.4 | 7 | 10 |
| 209391D | 6 | 1 | 1 | 83.2 | 7 | 10 |
| 209391E | 2 | 1 | 1 | 69.7 | 7 | 10 |
| 212022H | | | | 89.3 | 3 | 4 |
| 212023F | | | | 72.5 | 3 | 4 |
| 212027B | | | | 93.5 | 3 | 4 |
| 212910H | | | | 81.7 | 5 | 6 |
| 51443B | | | | 62.4 | 5 | 5 |
| 56800J | | | | 58.5 | 5 | 5 |
| 304474J | | | | 77 | 4 | 12 |
| 304475B | | | | 69 | 4 | 12 |
| 304476E | | | | 71.6 | 4 | 12 |

| Tester | ERTLPN % NOT ABS Mean | ERTLPN % NOT ABS Locs | ERTLPN % NOT ABS Reps | LRTLPN % NOT ABS Mean | LRTLPN % NOT ABS Locs | LRTLPN % NOT ABS Reps |
|---|---|---|---|---|---|---|
| 75231B | 100 | 1 | 1 | | | |
| 75229A | 90 | 1 | 1 | | | |
| 53300D | 76 | 4 | 5 | 75 | 7 | 8 |
| 56798D | 100 | 2 | 2 | 95 | 2 | 2 |
| 56807G | 100 | 2 | 2 | 77.5 | 2 | 2 |
| 57072E | 20 | 1 | 1 | 100 | 1 | 1 |
| 61682H | 100 | 1 | 1 | 61.7 | 3 | 3 |
| 75226A | 60 | 1 | 1 | 50 | 2 | 2 |
| 752263D | 70 | 2 | 2 | 77.5 | 4 | 4 |
| 209391B | 80 | 3 | 4 | 91 | 2 | 2 |
| 209391D | 80 | 3 | 4 | 88 | 4 | 4 |
| 209391E | 72.5 | 3 | 4 | 98.5 | 2 | 2 |
| 212022H | 60 | 3 | 3 | 93.3 | 3 | 3 |
| 212023F | 16.7 | 3 | 3 | 76.7 | 3 | 3 |
| 212027B | 43.3 | 3 | 3 | 63.3 | 3 | 3 |
| 212910H | | | | 80 | 3 | 4 |
| 51443B | 100 | 1 | 1 | 77.5 | 2 | 2 |
| 56800J | 100 | 2 | 2 | 82.5 | 2 | 2 |
| 304474J | 39.5 | 2 | 4 | 48.6 | 4 | 7 |
| 304475B | 48.8 | 2 | 4 | 41.4 | 4 | 7 |
| 304476E | 36.8 | 2 | 4 | 35 | 4 | 8 |

TABLE 5B

Combining Ability Report for Inbred PH87P
F1 data for Inbred Line PH87P when crossed to different tester lines than in Table 5A

| Tester | YIELD bu/a 56# ABS Mean | YIELD bu/a 56# ABS Locs | YIELD bu/a 56# ABS Reps | MST pct ABS Mean | MST pct ABS Locs | MST pct ABS Reps | EGRWTH score ABS Mean | EGRWTH score ABS Locs | EGRWTH score ABS Reps |
|---|---|---|---|---|---|---|---|---|---|
| 76014K | 176.4 | 17 | 17 | 23.4 | 17 | 17 | 6 | 1 | 1 |
| 76015A | 180.7 | 35 | 35 | 22.4 | 35 | 35 | 5 | 1 | 1 |
| 76031J | 169.9 | 17 | 17 | 21.4 | 17 | 17 | 9 | 1 | 1 |
| 76032B | 177.6 | 28 | 31 | 20.9 | 29 | 32 | 5 | 1 | 1 |
| 76032C | 184.6 | 17 | 17 | 23 | 17 | 17 | 6 | 1 | 1 |
| 76032D | 183.5 | 17 | 17 | 23.3 | 17 | 17 | 7 | 1 | 1 |
| 76032F | 180.1 | 17 | 17 | 22.7 | 17 | 17 | 7 | 1 | 1 |
| 76042C | 185.3 | 16 | 19 | 22.8 | 16 | 19 | | | |
| 76042F | 185.2 | 16 | 19 | 23.4 | 16 | 19 | | | |
| 76042H | 188.3 | 18 | 22 | 23.7 | 18 | 22 | | | |
| 212027G | 179.6 | 17 | 17 | 22.9 | 17 | 17 | | | |
| 212027K | 180.8 | 18 | 18 | 21.2 | 18 | 18 | | | |
| 212910E | 162.4 | 17 | 20 | 22.7 | 17 | 20 | | | |
| 53338E | 180.3 | 21 | 21 | 22.1 | 21 | 21 | 5.5 | 4 | 4 |
| 53576E | 182.8 | 147 | 239 | 22.4 | 149 | 241 | 5.8 | 17 | 22 |
| 61670G | 178.8 | 33 | 33 | 21.3 | 34 | 34 | 5.8 | 6 | 6 |
| 73323J | 200.7 | 29 | 32 | 20.5 | 30 | 33 | 6 | 2 | 2 |
| 76042K | 176.8 | 15 | 18 | 25.6 | 16 | 19 | | | |
| 212027J | 168.2 | 17 | 17 | 22.9 | 17 | 17 | | | |
| 49195B | 176.6 | 140 | 198 | 21.6 | 142 | 200 | 6.4 | 17 | 20 |
| 56803J | 183 | 20 | 20 | 20.2 | 20 | 20 | 6 | 4 | 4 |

TABLE 5B-continued

Combining Ability Report for Inbred PH87P
F1 data for Inbred Line PH87P when crossed to different tester lines than in Table 5A

| | | | | | | | | | |
|---|---|---|---|---|---|---|---|---|---|
| 76021B | 202.8 | 18 | 18 | 22.1 | 18 | 18 | 7 | 1 | 1 |
| 209401J | 157.7 | 21 | 22 | 21 | 21 | 22 | | | |
| 51420A | 193.4 | 27 | 31 | 21.7 | 27 | 31 | 5 | 2 | 2 |
| 51541K | 192.4 | 34 | 34 | 20.5 | 35 | 35 | 6.3 | 10 | 10 |
| 51443A | 176.7 | 20 | 20 | 20.7 | 20 | 20 | 5.5 | 4 | 4 |
| 304474F | 191.4 | 16 | 39 | 23.4 | 16 | 39 | | | |
| 75232C | 203.2 | 34 | 34 | 22 | 35 | 35 | 5.7 | 7 | 7 |

| Tester | ESTCNT count ABS Mean | ESTCNT count ABS Locs | ESTCNT count ABS Reps | GDUSHD GDU ABS Mean | GDUSHD GDU ABS Locs | GDUSHD GDU ABS Reps | GDUSLK GDU ABS Mean | GDUSLK GDU ABS Locs | GDUSLK GDU ABS Reps |
|---|---|---|---|---|---|---|---|---|---|
| 76014K | | | | 143.5 | 6 | 6 | 148.3 | 3 | 3 |
| 76015A | | | | 143.1 | 11 | 11 | 147.7 | 7 | 7 |
| 76031J | | | | 142.7 | 6 | 6 | 148.7 | 3 | 3 |
| 76032B | 51 | 5 | 10 | 145.5 | 5 | 5 | 148.5 | 4 | 4 |
| 76032C | | | | 139.5 | 6 | 6 | 148.3 | 3 | 3 |
| 76032D | | | | 138.7 | 6 | 6 | 146.3 | 3 | 3 |
| 76032F | | | | 142.7 | 6 | 6 | 145.3 | 3 | 3 |
| 76042C | | | | 142.8 | 4 | 4 | 142.5 | 2 | 2 |
| 76042F | | | | 144 | 4 | 4 | 145 | 2 | 2 |
| 76042H | | | | 145.5 | 2 | 2 | | | |
| 212027G | | | | 144.7 | 5 | 5 | 148.8 | 4 | 4 |
| 212027K | | | | 143.1 | 5 | 5 | 146.2 | 4 | 4 |
| 212910E | | | | 148.7 | 3 | 3 | 141 | 1 | 1 |
| 53338E | | | | 137.8 | 4 | 4 | 161 | 1 | 1 |
| 53576E | 56 | 13 | 35 | 143.8 | 37 | 73 | 146 | 26 | 46 |
| 61670G | | | | 140.5 | 10 | 10 | 137 | 3 | 3 |
| 73323J | 55.6 | 5 | 10 | 140.8 | 4 | 4 | 139 | 1 | 1 |
| 76042K | | | | 147.3 | 4 | 4 | 147.5 | 2 | 2 |
| 212027J | | | | 147.1 | 5 | 5 | 148 | 4 | 4 |
| 49195B | 56.1 | 13 | 34 | 145.6 | 33 | 53 | 148.4 | 24 | 38 |
| 56803J | | | | 139 | 4 | 4 | 147 | 1 | 1 |
| 76021B | | | | 140.8 | 4 | 4 | 133 | 1 | 1 |
| 209401J | | | | 134.7 | 5 | 6 | 139.5 | 2 | 2 |
| 51420A | | | | 143.5 | 4 | 4 | 136 | 1 | 1 |
| 51541K | | | | 138.6 | 9 | 9 | 142.5 | 2 | 2 |
| 51443A | | | | 136.8 | 4 | 4 | 147 | 1 | 1 |
| 304474F | 67.9 | 4 | 14 | 148.8 | 10 | 26 | 150.5 | 9 | 22 |
| 75232C | | | | 138.4 | 9 | 9 | 132.5 | 2 | 2 |

| Tester | PLTHT cm ABS Mean | PLTHT cm ABS Locs | PLTHT cm ABS Reps | EARHT cm ABS Mean | EARHT cm ABS Locs | EARHT cm ABS Reps | STAGRN score ABS Mean | STAGRN score ABS Locs | STAGRN score ABS Reps |
|---|---|---|---|---|---|---|---|---|---|
| 76014K | 308.9 | 5 | 5 | 129.5 | 5 | 5 | 3.7 | 3 | 3 |
| 76015A | 319.7 | 8 | 8 | 129.5 | 8 | 8 | 4.3 | 6 | 6 |
| 76031J | 297.2 | 5 | 5 | 108.2 | 5 | 5 | 3.3 | 3 | 3 |
| 76032B | 333.8 | 6 | 7 | 137.5 | 6 | 7 | 5 | 9 | 10 |
| 76032C | 308.4 | 5 | 5 | 117.9 | 5 | 5 | 5.7 | 3 | 3 |
| 76032D | 310.9 | 5 | 5 | 127.5 | 5 | 5 | 5 | 3 | 3 |
| 76032F | 306.3 | 5 | 5 | 121.4 | 5 | 5 | 4.7 | 3 | 3 |
| 76042C | 308.4 | 5 | 5 | 110.5 | 5 | 5 | 4.5 | 2 | 2 |
| 76042F | 306.3 | 5 | 5 | 117.9 | 5 | 5 | 5 | 2 | 2 |
| 76042H | 306.7 | 4 | 4 | 133.4 | 4 | 4 | 3 | 1 | 1 |
| 212027G | 322.6 | 3 | 3 | 137.2 | 3 | 3 | 6 | 3 | 3 |
| 212027K | 321.7 | 3 | 3 | 137.2 | 3 | 3 | 4.3 | 3 | 3 |
| 212910E | 325.1 | 3 | 3 | 132.1 | 3 | 3 | 2.8 | 5 | 6 |
| 53338E | 326 | 6 | 6 | 136.3 | 6 | 6 | 5.3 | 8 | 8 |
| 53576E | 299 | 41 | 80 | 118.5 | 41 | 80 | 4.8 | 39 | 67 |
| 61670G | 316.2 | 10 | 10 | 128.8 | 10 | 10 | 3.2 | 10 | 10 |
| 73323J | 328.6 | 7 | 8 | 141.9 | 7 | 8 | 4.6 | 13 | 14 |
| 76042K | 318.5 | 5 | 5 | 124 | 5 | 5 | 5.5 | 2 | 2 |
| 212027J | 325.1 | 3 | 3 | 147.3 | 3 | 3 | 5.3 | 3 | 3 |
| 49195B | 322 | 35 | 54 | 131.6 | 35 | 54 | 5.4 | 38 | 54 |
| 56803J | 322.6 | 6 | 6 | 143.5 | 6 | 6 | 5.3 | 8 | 8 |
| 76021B | 333.4 | 4 | 4 | 150.5 | 4 | 4 | 3.7 | 7 | 7 |
| 209401J | 285.8 | 4 | 4 | 114.3 | 4 | 4 | 4.3 | 4 | 4 |
| 51420A | 331.5 | 7 | 8 | 148 | 7 | 8 | 6.1 | 12 | 13 |
| 51541K | 314.7 | 11 | 11 | 132.3 | 11 | 11 | 4.1 | 16 | 16 |
| 51443A | 312 | 6 | 6 | 128.3 | 6 | 6 | 5 | 8 | 8 |
| 304474F | 273.8 | 6 | 20 | 108.5 | 6 | 20 | 4.4 | 7 | 18 |
| 75232C | 324.6 | 9 | 9 | 135.5 | 9 | 9 | 4.1 | 15 | 15 |

TABLE 5B-continued

Combining Ability Report for Inbred PH87P
F1 data for Inbred Line PH87P when crossed to different tester lines than in Table 5A

| Tester | TSTWT lb/bu ABS Mean | TSTWT lb/bu ABS Locs | TSTWT lb/bu ABS Reps | GLFSPT score ABS Mean | GLFSPT score ABS Locs | GLFSPT score ABS Reps | SLFBLT score ABS Mean | SLFBLT score ABS Locs | SLFBLT score ABS Reps |
|---|---|---|---|---|---|---|---|---|---|
| 76014K | 56.6 | 15 | 15 | | | | | | |
| 76015A | 56.8 | 31 | 31 | 5.5 | 2 | 2 | | | |
| 76031J | 57.5 | 15 | 15 | | | | | | |
| 76032B | 57.3 | 27 | 30 | 6 | 3 | 3 | | | |
| 76032C | 56.4 | 15 | 15 | | | | | | |
| 76032D | 57.3 | 15 | 15 | | | | | | |
| 76032F | 56.2 | 15 | 15 | | | | | | |
| 76042C | 56.8 | 16 | 19 | 6 | 1 | 1 | | | |
| 76042F | 56.3 | 16 | 19 | 6 | 1 | 1 | | | |
| 76042H | 56.6 | 18 | 22 | 7 | 1 | 1 | | | |
| 212027G | 57.3 | 15 | 15 | 7 | 2 | 2 | | | |
| 212027K | 57.1 | 16 | 16 | 5 | 2 | 2 | | | |
| 212910E | 57.5 | 17 | 19 | | | | | | |
| 53338E | 57.8 | 16 | 16 | 5 | 1 | 1 | | | |
| 53576E | 57.5 | 133 | 211 | 6 | 17 | 31 | 6.4 | 4 | 8 |
| 61670G | 57.2 | 31 | 31 | 4 | 1 | 1 | | | |
| 73323J | 56.8 | 27 | 30 | 6.3 | 3 | 3 | | | |
| 76042K | 56.6 | 16 | 19 | 7 | 1 | 1 | | | |
| 212027J | 57.3 | 16 | 16 | 6 | 1 | 1 | | | |
| 49195B | 57.7 | 126 | 178 | 7 | 16 | 26 | 5.9 | 4 | 8 |
| 56803J | 57.5 | 15 | 15 | | | | | | |
| 76021B | 57.4 | 15 | 15 | 6 | 2 | 2 | | | |
| 209401J | 58.8 | 13 | 14 | 7 | 1 | 1 | | | |
| 51420A | 57.5 | 21 | 24 | 6.3 | 3 | 4 | 8 | 2 | 2 |
| 51541K | 56.8 | 30 | 30 | 4 | 1 | 1 | | | |
| 51443A | 58.7 | 15 | 15 | | | | | | |
| 304474F | 56.8 | 14 | 33 | 5.8 | 2 | 4 | | | |
| 75232C | 56.7 | 31 | 31 | 5.7 | 3 | 3 | | | |

| Tester | ANTROT score ABS Mean | ANTROT score ABS Locs | ANTROT score ABS Reps | SOURST score ABS Mean | SOURST score ABS Locs | SOURST score ABS Reps | ECB2SC score ABS Mean | ECB2SC score ABS Locs | ECB2SC score ABS Reps |
|---|---|---|---|---|---|---|---|---|---|
| 76014K | | | | | | | 9 | 2 | 2 |
| 76015A | | | | | | | 9 | 3 | 3 |
| 76031J | | | | | | | 7 | 2 | 2 |
| 76032B | | | | 2 | 1 | 2 | | | |
| 76032C | | | | | | | 8 | 2 | 2 |
| 76032D | | | | | | | 8 | 2 | 2 |
| 76032F | | | | | | | 7 | 2 | 2 |
| 76042C | | | | | | | | | |
| 76042F | | | | | | | | | |
| 76042H | | | | | | | | | |
| 212027G | | | | | | | 9 | 1 | 1 |
| 212027K | | | | | | | 9 | 1 | 1 |
| 212910E | | | | | | | | | |
| 53338E | | | | | | | | | |
| 53576E | 4.5 | 8 | 22 | 1.7 | 1 | 3 | 5.3 | 11 | 21 |
| 61670G | | | | | | | | | |
| 73323J | | | | 2 | 1 | 2 | | | |
| 76042K | | | | | | | | | |
| 212027J | | | | | | | 9 | 1 | 1 |
| 49195B | 4.9 | 8 | 24 | 4.7 | 1 | 3 | 5.4 | 10 | 19 |
| 56803J | | | | | | | | | |
| 76021B | | | | | | | | | |
| 209401J | 4 | 1 | 1 | | | | 7 | 1 | 1 |
| 51420A | 4.5 | 2 | 2 | | | | | | |
| 51541K | | | | | | | | | |
| 51443A | | | | | | | | | |
| 304474F | | | | | | | 9 | 1 | 2 |
| 75232C | | | | | | | | | |

| Tester | GIBROT score ABS Mean | GIBROT score ABS Locs | GIBROT score ABS Reps | BRTSTK % NOT ABS Mean | BRTSTK % NOT ABS Locs | BRTSTK % NOT ABS Reps | STLLPN % NOT ABS Mean | STLLPN % NOT ABS Locs | STLLPN % NOT ABS Reps |
|---|---|---|---|---|---|---|---|---|---|
| 76014K | | | | | | | 70.7 | 6 | 6 |
| 76015A | | | | | | | 77 | 9 | 10 |
| 76031J | | | | | | | 56.4 | 6 | 6 |
| 76032B | | | | | | | 95.7 | 6 | 9 |
| 76032C | | | | | | | 76.4 | 6 | 6 |

TABLE 5B-continued

Combining Ability Report for Inbred PH87P
F1 data for Inbred Line PH87 when crossed to different tester lines than in Table 5A

| | | | | | | | | | |
|---|---|---|---|---|---|---|---|---|---|
| 76032D | | | | | | | 58.9 | 6 | 6 |
| 76032F | | | | | | | 64.4 | 6 | 6 |
| 76042C | | | | | | | 78.5 | 4 | 4 |
| 76042F | | | | | | | 73.6 | 5 | 5 |
| 76042H | | | | | | | 89.4 | 4 | 4 |
| 212027G | | | | | | | 87.5 | 3 | 4 |
| 212027K | | | | | | | 89.3 | 3 | 4 |
| 212910E | | | | | | | 72 | 3 | 5 |
| 53338E | | | | | | | 69.3 | 5 | 5 |
| 53576E | 4.6 | 3 | 8 | 98.9 | 3 | 4 | 75 | 25 | 73 |
| 61670G | | | | 100 | 1 | 1 | 75.8 | 8 | 8 |
| 73323J | | | | | | | 80.1 | 8 | 10 |
| 76042K | | | | | | | 80.3 | 5 | 5 |
| 212027J | | | | | | | 82.3 | 3 | 4 |
| 49195B | 6 | 3 | 8 | 100 | 3 | 4 | 80.6 | 23 | 59 |
| 56803J | | | | | | | 87.5 | 4 | 4 |
| 76021B | | | | | | | 56 | 5 | 5 |
| 209401J | 8.5 | 1 | 2 | | | | 88 | 2 | 4 |
| 51420A | | | | | | | 68.8 | 7 | 8 |
| 51541K | | | | 100 | 1 | 1 | 68.7 | 7 | 7 |
| 51443A | | | | | | | 73.1 | 4 | 4 |
| 304474F | | | | | | | 78.3 | 4 | 12 |
| 75232C | | | | 94.2 | 1 | 1 | 70.7 | 8 | 8 |

| Tester | ABTSTK % NOT ABS Mean | ABTSTK % NOT ABS Locs | ABTSTK % NOT ABS Reps | ERTLPN % NOT ABS Mean | ERTLPN % NOT ABS Locs | ERTLPN % NOT ABS Reps | LRTLPN % NOT ABS Mean | LRTLPN % NOT ABS Locs | LRTLPN % NOT ABS Reps |
|---|---|---|---|---|---|---|---|---|---|
| 76014K | | | | 90 | 1 | 1 | 56.7 | 3 | 3 |
| 76015A | | | | 77.5 | 4 | 4 | 89.2 | 6 | 6 |
| 76031J | | | | 90 | 1 | 1 | 86.7 | 3 | 3 |
| 76032B | | | | 91.4 | 6 | 7 | 90 | 3 | 3 |
| 76032C | | | | 80 | 1 | 1 | 65 | 3 | 3 |
| 76032D | | | | 90 | 1 | 1 | 41.7 | 3 | 3 |
| 76032F | | | | 100 | 1 | 1 | 78.3 | 3 | 3 |
| 76042C | | | | 100 | 1 | 1 | | | |
| 76042F | | | | 90 | 1 | 1 | | | |
| 76042H | | | | 95 | 2 | 2 | 100 | 1 | 1 |
| 212027G | | | | 33.3 | 3 | 3 | 93.3 | 3 | 3 |
| 212027K | | | | 66.7 | 3 | 3 | 43.3 | 3 | 3 |
| 212910E | | | | | | | 66 | 4 | 5 |
| 53338E | 66.7 | 2 | 4 | | | | | | |
| 53576E | 56 | 6 | 30 | 77.5 | 10 | 18 | 78.4 | 16 | 25 |
| 61670G | | | | 30 | 1 | 1 | 100 | 1 | 1 |
| 73323J | | | | 98.3 | 5 | 6 | 72.5 | 2 | 2 |
| 76042K | | | | 100 | 1 | 1 | | | |
| 212027J | | | | 86.7 | 3 | 3 | 70 | 3 | 3 |
| 49195B | 70.1 | 6 | 30 | 85.9 | 9 | 16 | 81.6 | 16 | 22 |
| 56803J | 71.9 | 2 | 4 | | | | | | |
| 76021B | | | | 100 | 2 | 2 | 70 | 2 | 2 |
| 209401J | | | | 93 | 2 | 3 | 80 | 2 | 2 |
| 51420A | | | | 87.5 | 4 | 4 | 85 | 2 | 2 |
| 51541K | 72.9 | 2 | 4 | | | | | | |
| 51443A | 51.3 | 2 | 4 | | | | | | |
| 304474F | | | | 53 | 2 | 4 | 38.8 | 4 | 8 |
| 75232C | | | | 60 | 2 | 2 | 80 | 2 | 2 |

TABLE 6A

INBREDS IN HYBRID COMBINATION REPORT
Variety #1: HYBRID CONTAINING PH87P - Variety #2: 33J24

| Stat | YIELD BU/A 56# ABS | YIELD BU/A 56# % MN | MST PCT % MN | EGRWTH SCORE % MN | ESTCNT COUNT % MN | GDUSHD GDU % MN | GDUSLK GDU % MN |
|---|---|---|---|---|---|---|---|
| Mean1 | 189.9 | 102.6 | 103.4 | 92.9 | 96.0 | 100.1 | 100.7 |
| Mean2 | 180.1 | 97.1 | 96.8 | 105.0 | 100.8 | 99.1 | 98.0 |
| Locs | 135 | 135 | 137 | 16 | 11 | 32 | 23 |
| Reps | 138 | 138 | 140 | 16 | 15 | 39 | 28 |
| Diff | 9.8 | 5.5 | −6.7 | −12.1 | −4.8 | 1.0 | 2.6 |
| Prob | 0.000 | 0.000 | 0.000 | 0.026 | 0.009 | 0.011 | 0.002 |

TABLE 6A-continued

INBREDS IN HYBRID COMBINATION REPORT
Variety #1: HYBRID CONTAINING PH87P - Variety #2: 33J24

| Stat | STKCNT COUNT % MN | PLTHT CM % MN | EARHT CM % MN | STAGRN SCORE % MN | LRTLSC SCORE ABS | STKLDS SCORE ABS | STKLDG % NOT % MN |
|---|---|---|---|---|---|---|---|
| Mean1 | 99.3 | 97.0 | 94.3 | 110.2 | 7.0 | 8.2 | 98.3 |
| Mean2 | 100.3 | 94.9 | 91.0 | 106.1 | 8.0 | 6.8 | 102.6 |
| Locs | 217 | 31 | 31 | 36 | 1 | 13 | 4 |
| Reps | 300 | 35 | 35 | 37 | 1 | 13 | 5 |
| Diff | −1.0 | 2.1 | 3.4 | 4.1 | −1.0 | 1.3 | −4.2 |
| Prob | 0.026 | 0.034 | 0.129 | 0.580 | | 0.012 | 0.561 |

| Stat | ABTSTK % NOT % MN | TSTWT LB/BU ABS | GLFSPT SCORE ABS | NLFBLT SCORE ABS | SLFBLT SCORE ABS | ANTROT SCORE ABS | CLN SCORE ABS |
|---|---|---|---|---|---|---|---|
| Mean1 | 103.7 | 57.3 | 6.0 | 4.4 | 6.4 | 4.7 | 4.5 |
| Mean2 | 69.9 | 57.9 | 5.5 | 6.5 | 6.0 | 5.1 | 4.5 |
| Locs | 6 | 98 | 14 | 5 | 4 | 8 | 1 |
| Reps | 30 | 101 | 18 | 9 | 6 | 16 | 4 |
| Diff | 33.8 | −0.6 | 0.5 | −2.1 | 0.4 | −0.4 | 0.0 |
| Prob | 0.000 | 0.000 | 0.050 | 0.001 | 0.671 | 0.677 | |

| Stat | MDMCPX SCORE ABS | FUSERS SCORE ABS | DIPERS SCORE ABS | SOURST SCORE ABS | ECBDPE % NOT ABS | ECB1LF SCORE ABS | ECB2SC SCORE ABS |
|---|---|---|---|---|---|---|---|
| Mean1 | 2.3 | 6.4 | 3.2 | 3.0 | 95.9 | 3.7 | 5.7 |
| Mean2 | 3.8 | 4.1 | 3.0 | 3.0 | 97.3 | 3.0 | 5.2 |
| Locs | 2 | 8 | 3 | 1 | 1 | 2 | 11 |
| Reps | 4 | 14 | 6 | 1 | 1 | 6 | 16 |
| Diff | −1.5 | 2.3 | 0.2 | 0.0 | −1.4 | 0.7 | 0.4 |
| Prob | 0.205 | 0.004 | 0.742 | | | 0.295 | 0.234 |

| Stat | HSKCVR SCORE ABS | GIBROT SCORE ABS | DIPROT SCORE ABS | BRTSTK % NOT ABS | HD SMT % NOT ABS | ERTLPN % NOT ABS | LRTLPN % NOT ABS |
|---|---|---|---|---|---|---|---|
| Mean1 | 6.1 | 4.8 | 3.0 | 98.7 | 93.0 | 82.3 | 86.8 |
| Mean2 | 4.9 | 4.5 | 8.5 | 97.4 | 98.7 | 80.4 | 93.9 |
| Locs | 12 | 2 | 1 | 2 | 5 | 12 | 19 |
| Reps | 12 | 4 | 2 | 2 | 7 | 16 | 20 |
| Diff | 1.2 | 0.3 | −5.5 | 1.3 | −5.7 | 1.9 | −7.1 |
| Prob | 0.004 | 0.874 | | 0.500 | 0.097 | 0.779 | 0.168 |

TABLE 6B

INBREDS IN HYBRID COMBINATION REPORT
Variety #1: HYBRID CONTAINING PH87P - Variety #2: 32W86

| Stat | YIELD BU/A 56# ABS | YIELD BU/A 56# % MN | MST PCT % MN | EGRWTH SCORE % MN | ESTCNT COUNT % MN | GDUSHD GDU % MN | GDUSLK GDU % MN |
|---|---|---|---|---|---|---|---|
| Mean1 | 184.2 | 100.6 | 101.9 | 91.8 | 100.0 | 100.7 | 101.2 |
| Mean2 | 193.6 | 105.5 | 101.3 | 93.6 | 99.1 | 100.9 | 101.3 |
| Locs | 161 | 161 | 162 | 13 | 21 | 40 | 33 |
| Reps | 207 | 207 | 208 | 16 | 35 | 53 | 42 |
| Diff | −9.3 | −4.9 | −0.5 | −1.8 | 1.0 | −0.1 | −0.1 |
| Prob | 0.000 | 0.000 | 0.345 | 0.723 | 0.656 | 0.724 | 0.751 |

| Stat | STKCNT COUNT % MN | PLTHT CM % MN | EARHT CM % MN | STAGRN SCORE % MN | STKLDG % NOT % MN | ABTSTK % NOT % MN | TSTWT LB/BU ABS |
|---|---|---|---|---|---|---|---|
| Mean1 | 99.7 | 97.1 | 93.1 | 100.9 | 97.1 | 103.7 | 57.6 |
| Mean2 | 100.6 | 105.0 | 102.9 | 99.0 | 96.7 | 87.8 | 57.3 |
| Locs | 273 | 41 | 41 | 40 | 3 | 6 | 123 |
| Reps | 433 | 57 | 57 | 51 | 4 | 30 | 161 |
| Diff | −0.9 | −7.8 | −9.8 | 1.9 | 0.4 | 15.9 | 0.2 |
| Prob | 0.010 | 0.000 | 0.000 | 0.687 | 0.973 | 0.137 | 0.188 |

TABLE 6B-continued

INBREDS IN HYBRID COMBINATION REPORT
Variety #1: HYBRID CONTAINING PH87P - Variety #2: 32W86

| Stat | GLFSPT SCORE ABS | NLFBLT SCORE ABS | SLFBLT SCORE ABS | ANTROT SCORE ABS | CLN SCORE ABS | MDMCPX SCORE ABS | FUSERS SCORE ABS |
|---|---|---|---|---|---|---|---|
| Mean1 | 6.2 | 4.4 | 6.5 | 4.5 | 4.5 | 2.3 | 6.4 |
| Mean2 | 5.6 | 4.8 | 5.4 | 4.2 | 4.0 | 2.5 | 5.4 |
| Locs | 18 | 7 | 5 | 11 | 1 | 2 | 11 |
| Reps | 27 | 12 | 8 | 22 | 4 | 4 | 19 |
| Diff | 0.5 | −0.4 | 1.1 | 0.3 | 0.5 | −0.3 | 1.0 |
| Prob | 0.012 | 0.172 | 0.180 | 0.432 | | 0.500 | 0.035 |

| Stat | DIPERS SCORE ABS | SOURST SCORE ABS | ECBDPE % NOT ABS | ECB1LF SCORE ABS | ECB2SC SCORE ABS | HSKCVR SCORE ABS | GIBROT SCORE ABS |
|---|---|---|---|---|---|---|---|
| Mean1 | 3.6 | 2.0 | 97.6 | 3.9 | 5.5 | 6.0 | 4.6 |
| Mean2 | 3.4 | 3.3 | 98.9 | 2.9 | 5.7 | 5.2 | 3.6 |
| Locs | 4 | 2 | 2 | 5 | 16 | 15 | 4 |
| Reps | 8 | 3 | 3 | 12 | 26 | 17 | 8 |
| Diff | 0.3 | −1.3 | −1.3 | 1.0 | −0.1 | 0.7 | 1.0 |
| Prob | 0.731 | 0.126 | 0.716 | 0.012 | 0.609 | 0.005 | 0.139 |

| Stat | DIPROT SCORE ABS | CEWEDM SCORE ABS | BRTSTK % NOT ABS | HD SMT % NOT ABS | ERTLPN % NOT ABS | LRTLPN % NOT ABS | SWBPGR % NOT ABS |
|---|---|---|---|---|---|---|---|
| Mean1 | 3.0 | 4.5 | 98.3 | 94.2 | 79.5 | 84.8 | 72.0 |
| Mean2 | 3.8 | 4.0 | 92.6 | 95.3 | 81.4 | 79.6 | 34.0 |
| Locs | 2 | 1 | 2 | 6 | 16 | 24 | 2 |
| Reps | 4 | 2 | 3 | 9 | 22 | 29 | 4 |
| Diff | −0.8 | 0.5 | 5.6 | −1.1 | −1.9 | 5.2 | 38.0 |
| Prob | 0.500 | | 0.043 | 0.491 | 0.587 | 0.332 | 0.054 |

TABLE 6C

INBREDS IN HYBRID COMBINATION REPORT
Variety #1: HYBRID CONTAINING PH87P - Variety #2: 32D12

| Stat | YIELD BU/A 56# ABS | YIELD BU/A 56# % MN | MST PCT % MN | EGRWTH SCORE % MN | ESTCNT COUNT % MN | GDUSHD GDU % MN | GDUSLK GDU % MN | STKCNT COUNT % MN | PLTHT CM % MN |
|---|---|---|---|---|---|---|---|---|---|
| Mean1 | 186.7 | 101.0 | 103.3 | 87.5 | 96.0 | 101.0 | 101.5 | 99.0 | 96.6 |
| Mean2 | 186.3 | 100.9 | 99.1 | 90.9 | 104.0 | 100.1 | 99.2 | 100.7 | 97.2 |
| Locs | 118 | 118 | 119 | 10 | 11 | 30 | 25 | 202 | 28 |
| Reps | 121 | 121 | 122 | 10 | 15 | 37 | 30 | 294 | 33 |
| Diff | 0.4 | 0.1 | −4.2 | −3.3 | −8.0 | 0.9 | 2.3 | −1.7 | −0.5 |
| Prob | 0.868 | 0.948 | 0.000 | 0.632 | 0.002 | 0.019 | 0.002 | 0.000 | 0.569 |

| Stat | EARHT CM % MN | STAGRN SCORE % MN | STKLDG % NOT % MN | ABTSTK % NOT % MN | TSTWT LB/BU ABS | GLFSPT SCORE ABS | NLFBLT SCORE ABS | SLFBLT SCORE ABS | ANTROT SCORE ABS |
|---|---|---|---|---|---|---|---|---|---|
| Mean1 | 93.6 | 107.1 | 97.1 | 103.7 | 57.4 | 6.2 | 4.4 | 6.4 | 4.7 |
| Mean2 | 98.8 | 101.5 | 87.9 | 96.3 | 56.9 | 6.0 | 5.7 | 6.4 | 4.4 |
| Locs | 28 | 28 | 3 | 6 | 85 | 13 | 5 | 4 | 8 |
| Reps | 33 | 29 | 4 | 29 | 88 | 17 | 9 | 6 | 14 |
| Diff | −5.1 | 5.6 | 9.1 | 7.4 | 0.5 | 0.2 | −1.3 | 0.0 | 0.3 |
| Prob | 0.020 | 0.206 | 0.325 | 0.524 | 0.028 | 0.351 | 0.007 | 1.000 | 0.725 |

| Stat | CLN SCORE ABS | MDMCPX SCORE ABS | FUSERS SCORE ABS | DIPERS SCORE ABS | SOURST SCORE ABS | ECBDPE % NOT ABS | ECB1LF SCORE ABS | ECB2SC SCORE ABS | HSKCVR SCORE ABS |
|---|---|---|---|---|---|---|---|---|---|
| Mean1 | 4.5 | 2.3 | 6.4 | 3.2 | 3.0 | 95.9 | 3.7 | 5.7 | 6.1 |
| Mean2 | 3.0 | 2.3 | 4.9 | 4.0 | 4.0 | 98.6 | 2.7 | 4.9 | 5.5 |
| Locs | 1 | 2 | 8 | 3 | 1 | 1 | 2 | 11 | 12 |
| Reps | 4 | 4 | 14 | 6 | 1 | 1 | 6 | 16 | 12 |
| Diff | 1.5 | 0.0 | 1.5 | −0.8 | −1.0 | −2.7 | 1.0 | 0.7 | 0.6 |
| Prob | | 1.000 | 0.023 | 0.038 | | | 0.374 | 0.125 | 0.111 |

TABLE 6C-continued

INBREDS IN HYBRID COMBINATION REPORT
Variety #1: HYBRID CONTAINING PH87P - Variety #2: 32D12

| Stat | GIBROT SCORE ABS | DIPROT SCORE ABS | BRTSTK % NOT ABS | HD SMT % NOT ABS | ERTLPN % NOT ABS | LRTLPN % NOT ABS |
|---|---|---|---|---|---|---|
| Mean1 | 4.8 | 3.0 | 98.3 | 93.0 | 82.3 | 86.8 |
| Mean2 | 3.0 | 7.0 | 100.0 | 97.3 | 83.5 | 86.6 |
| Locs | 2 | 1 | 2 | 5 | 12 | 19 |
| Reps | 4 | 2 | 3 | 7 | 16 | 20 |
| Diff | 1.8 | −4.0 | −1.7 | −4.3 | −1.3 | 0.3 |
| Prob | 0.090 |  | 0.299 | 0.332 | 0.806 | 0.961 |

TABLE 6D

INBREDS IN HYBRID COMBINATION REPORT
Variety #1: HYBRID CONTAINING PH87P-different from hybrid in Tables 6A–6C
Variety #2: 33J24

| Stat | YIELD BU/A 56# ABS | YIELD BU/A 56# % MN | MST PCT % MN | EGRWTH SCORE % MN | ESTCNT COUNT % MN | GDUSHD GDU % MN | GDUSLK GDU % MN |
|---|---|---|---|---|---|---|---|
| Mean1 | 185.3 | 100.0 | 100.7 | 110.2 | 98.0 | 101.5 | 102.5 |
| Mean2 | 180.5 | 97.2 | 96.7 | 105.0 | 100.8 | 99.1 | 98.0 |
| Locs | 135 | 135 | 137 | 16 | 11 | 32 | 23 |
| Reps | 139 | 139 | 141 | 16 | 14 | 39 | 28 |
| Diff | 4.9 | 2.8 | −4.0 | 5.2 | −2.8 | 2.4 | 4.5 |
| Prob | 0.019 | 0.030 | 0.000 | 0.400 | 0.172 | 0.000 | 0.000 |

| Stat | STKCNT COUNT % MN | PLTHT CM % MN | EARHT CM % MN | STAGRN SCORE % MN | LRTLSC SCORE ABS | STKLDS SCORE ABS | STKLDG % NOT % MN |
|---|---|---|---|---|---|---|---|
| Mean1 | 100.1 | 102.0 | 100.7 | 118.5 | 7.0 | 7.3 | 105.6 |
| Mean2 | 100.3 | 94.9 | 91.0 | 106.1 | 8.0 | 6.7 | 102.6 |
| Locs | 215 | 31 | 31 | 36 | 1 | 12 | 4 |
| Reps | 299 | 35 | 35 | 37 | 1 | 12 | 5 |
| Diff | −0.2 | 7.1 | 9.7 | 12.4 | −1.0 | 0.7 | 3.0 |
| Prob | 0.552 | 0.000 | 0.003 | 0.159 |  | 0.039 | 0.212 |

| Stat | ABTSTK % NOT % MN | TSTWT LB/BU ABS | GLFSPT SCORE ABS | NLFBLT SCORE ABS | SLFBLT SCORE ABS | ANTROT SCORE ABS | CLN SCORE ABS |
|---|---|---|---|---|---|---|---|
| Mean1 | 125.1 | 57.6 | 6.9 | 5.5 | 5.6 | 4.6 | 5.5 |
| Mean2 | 69.9 | 57.9 | 5.5 | 6.5 | 6.0 | 5.1 | 4.5 |
| Locs | 6 | 96 | 13 | 5 | 4 | 8 | 1 |
| Reps | 30 | 100 | 17 | 9 | 6 | 17 | 4 |
| Diff | 55.2 | −0.3 | 1.4 | −1.0 | −0.4 | −0.5 | 1.0 |
| Prob | 0.002 | 0.051 | 0.000 | 0.022 | 0.215 | 0.531 |  |

| Stat | MDMCPX SCORE ABS | FUSERS SCORE ABS | DIPERS SCORE ABS | SOURST SCORE ABS | ECBDPE % NOT ABS | ECB1LF SCORE ABS | ECB2SC SCORE ABS |
|---|---|---|---|---|---|---|---|
| Mean1 | 2.8 | 6.6 | 3.0 | 6.0 | 95.9 | 4.8 | 4.9 |
| Mean2 | 3.8 | 4.1 | 3.0 | 3.0 | 97.3 | 3.0 | 5.2 |
| Locs | 2 | 8 | 3 | 1 | 1 | 2 | 11 |
| Reps | 4 | 14 | 6 | 1 | 1 | 6 | 16 |
| Diff | −1.0 | 2.5 | 0.0 | 3.0 | −1.4 | 1.8 | −0.3 |
| Prob | 0.295 | 0.002 | 1.000 |  |  | 0.058 | 0.447 |

| Stat | HSKCVR SCORE ABS | GIBROT SCORE ABS | DIPROT SCORE ABS | BRTSTK % NOT ABS | HD SMT % NOT ABS | ERTLPN % NOT ABS | LRTLPN % NOT ABS |
|---|---|---|---|---|---|---|---|
| Mean1 | 6.2 | 6.0 | 5.0 | 100.0 | 95.0 | 88.1 | 89.2 |
| Mean2 | 4.9 | 4.5 | 8.5 | 97.4 | 98.7 | 80.4 | 93.9 |
| Locs | 12 | 2 | 1 | 2 | 5 | 12 | 19 |
| Reps | 12 | 4 | 2 | 2 | 7 | 16 | 21 |
| Diff | 1.3 | 1.5 | −3.5 | 2.6 | −3.6 | 7.7 | −4.7 |
| Prob | 0.000 | 0.205 |  | 0.500 | 0.303 | 0.165 | 0.049 |

TABLE 6E

INBREDS IN HYBRID COMBINATION REPORT
Variety #1: HYBRID CONTAINING PH87P-different from hybrid in Tables 6A–6C
Variety #2: 32D12

| Stat | YIELD BU/A 56# ABS | YIELD BU/A 56# % MN | MST PCT % MN | EGRWTH SCORE % MN | ESTCNT COUNT % MN | GDUSHD GDU % MN | GDUSLK GDU % MN | STKCNT COUNT % MN | PLTHT CM % MN |
|---|---|---|---|---|---|---|---|---|---|
| Mean1 | 182.9 | 98.8 | 100.6 | 112.0 | 98.0 | 102.6 | 103.6 | 99.9 | 102.4 |
| Mean2 | 186.3 | 100.6 | 99.2 | 90.9 | 104.0 | 100.1 | 99.2 | 100.7 | 97.2 |
| Locs | 119 | 119 | 120 | 10 | 11 | 30 | 25 | 201 | 28 |
| Reps | 124 | 124 | 125 | 10 | 14 | 37 | 30 | 294 | 34 |
| Diff | −3.4 | −1.9 | −1.4 | 21.1 | −5.9 | 2.5 | 4.3 | −0.8 | 5.2 |
| Prob | 0.096 | 0.108 | 0.045 | 0.032 | 0.006 | 0.000 | 0.000 | 0.028 | 0.000 |

| Stat | EARHT CM % MN | STAGRN SCORE % MN | STKLDG % NOT % MN | ABTSTK % NOT % MN | TSTWT LB/BU ABS | GLFSPT SCORE ABS | NLFBLT SCORE ABS | SLFBLT SCORE ABS | ANTROT SCORE ABS |
|---|---|---|---|---|---|---|---|---|---|
| Mean1 | 102.3 | 113.2 | 107.4 | 125.1 | 57.6 | 6.9 | 5.5 | 5.6 | 4.6 |
| Mean2 | 98.8 | 101.5 | 87.9 | 96.3 | 56.8 | 6.0 | 5.7 | 6.4 | 4.4 |
| Locs | 28 | 28 | 3 | 6 | 84 | 13 | 5 | 4 | 8 |
| Reps | 34 | 30 | 4 | 29 | 89 | 17 | 9 | 6 | 14 |
| Diff | 3.6 | 11.7 | 19.4 | 28.8 | 0.7 | 1.0 | −0.2 | −0.8 | 0.2 |
| Prob | 0.050 | 0.048 | 0.319 | 0.165 | 0.001 | 0.002 | 0.621 | 0.182 | 0.779 |

| Stat | CLN SCORE ABS | MDMCPX SCORE ABS | FUSERS SCORE ABS | DIPERS SCORE ABS | SOURST SCORE ABS | ECBDPE % NOT ABS | ECB1LF SCORE ABS | ECB2SC SCORE ABS | HSKCVR SCORE ABS |
|---|---|---|---|---|---|---|---|---|---|
| Mean1 | 5.5 | 2.8 | 6.6 | 3.0 | 6.0 | 95.9 | 4.8 | 4.9 | 6.2 |
| Mean2 | 3.0 | 2.3 | 4.9 | 4.0 | 4.0 | 98.6 | 2.7 | 4.9 | 5.5 |
| Locs | 1 | 2 | 8 | 3 | 1 | 1 | 2 | 11 | 12 |
| Reps | 4 | 4 | 14 | 6 | 1 | 1 | 6 | 16 | 12 |
| Diff | 2.5 | 0.5 | 1.8 | −1.0 | 2.0 | −2.7 | 2.2 | 0.0 | 0.7 |
| Prob |  | 1.000 | 0.011 | 0.423 |  |  | 0.144 | 0.932 | 0.087 |

| Stat | GIBROT SCORE ABS | DIPROT SCORE ABS | BRTSTK % NOT ABS | HD SMT % NOT ABS | ERTLPN % NOT ABS | LRTLPN % NOT ABS |
|---|---|---|---|---|---|---|
| Mean1 | 6.0 | 5.0 | 100.0 | 95.0 | 88.1 | 89.2 |
| Mean2 | 3.0 | 7.0 | 100.0 | 97.3 | 83.5 | 86.6 |
| Locs | 2 | 1 | 2 | 5 | 12 | 19 |
| Reps | 4 | 2 | 3 | 7 | 16 | 21 |
| Diff | 3.0 | −2.0 | 0.0 | −2.2 | 4.6 | 2.6 |
| Prob | 0.295 |  | 1.000 | 0.120 | 0.160 | 0.501 |

TABLE 6F

INBREDS IN HYBRID COMBINATION REPORT
Variety #1: HYBRID CONTAINING PH87P different from hybrid in Tables 6A–6C
Variety #2: 32W86

| Stat | YIELD BU/A 56# ABS | YIELD BU/A 56# % MN | MST PCT % MN | EGRWTH SCORE % MN | ESTCNT COUNT % MN | GDUSHD GDU % MN | GDUSLK GDU % MN |
|---|---|---|---|---|---|---|---|
| Mean1 | 180.5 | 98.5 | 100.3 | 111.2 | 100.7 | 102.6 | 103.3 |
| Mean2 | 193.9 | 105.4 | 101.3 | 93.6 | 99.1 | 100.9 | 101.3 |
| Locs | 163 | 163 | 164 | 13 | 21 | 40 | 33 |
| Reps | 208 | 208 | 209 | 16 | 34 | 53 | 42 |
| Diff | −13.4 | −7.0 | 1.0 | 17.7 | 1.6 | 1.7 | 2.0 |
| Prob | 0.000 | 0.000 | 0.047 | 0.021 | 0.455 | 0.000 | 0.000 |

| Stat | STKCNT COUNT % MN | PLTHT CM % MN | EARHT CM % MN | STAGRN SCORE % MN | STKLDG % NOT % MN | ABTSTK % NOT % MN | TSTWT LB/BU ABS |
|---|---|---|---|---|---|---|---|
| Mean1 | 100.5 | 103.3 | 102.3 | 114.8 | 107.4 | 125.1 | 57.6 |
| Mean2 | 100.6 | 105.0 | 102.9 | 99.0 | 96.7 | 87.8 | 57.3 |
| Locs | 272 | 41 | 41 | 40 | 3 | 6 | 122 |
| Reps | 434 | 58 | 58 | 52 | 4 | 30 | 163 |
| Diff | −0.1 | −1.7 | −0.6 | 15.8 | 10.7 | 37.3 | 0.4 |
| Prob | 0.839 | 0.064 | 0.659 | 0.004 | 0.043 | 0.009 | 0.019 |

TABLE 6F-continued

INBREDS IN HYBRID COMBINATION REPORT
Variety #1: HYBRID CONTAINING PH87P different from hybrid in Tables 6A-6C
Variety #2: 32W86

| Stat | GLFSPT SCORE ABS | NLFBLT SCORE ABS | SLFBLT SCORE ABS | ANTROT SCORE ABS | CLN SCORE ABS | MDMCPX SCORE ABS | FUSERS SCORE ABS |
|---|---|---|---|---|---|---|---|
| Mean1 | 7.0 | 5.3 | 5.8 | 4.7 | 5.5 | 2.8 | 6.9 |
| Mean2 | 5.6 | 4.8 | 5.4 | 4.2 | 4.0 | 2.5 | 5.4 |
| Locs | 18 | 7 | 5 | 11 | 1 | 2 | 11 |
| Reps | 26 | 12 | 8 | 22 | 4 | 4 | 19 |
| Diff | 1.4 | 0.5 | 0.4 | 0.5 | 1.5 | 0.3 | 1.5 |
| Prob | 0.000 | 0.309 | 0.405 | 0.263 | | 0.500 | 0.003 |

| Stat | DIPERS SCORE ABS | SOURST SCORE ABS | ECBDPE % NOT ABS | ECB1LF SCORE ABS | ECB2SC SCORE ABS | HSKCVR SCORE ABS | GIBROT SCORE ABS |
|---|---|---|---|---|---|---|---|
| Mean1 | 3.3 | 5.0 | 96.5 | 4.5 | 5.1 | 5.9 | 6.0 |
| Mean2 | 3.4 | 3.3 | 98.9 | 2.9 | 5.7 | 5.2 | 3.6 |
| Locs | 4 | 2 | 2 | 5 | 16 | 15 | 4 |
| Reps | 8 | 3 | 3 | 12 | 26 | 17 | 8 |
| Diff | −0.1 | 1.8 | −2.4 | 1.7 | −0.6 | 0.7 | 2.4 |
| Prob | 0.761 | 0.090 | 0.389 | 0.031 | 0.138 | 0.001 | 0.023 |

| Stat | DIPROT SCORE ABS | CEWEDM SCORE ABS | BRTSTK % NOT ABS | HD SMT % NOT ABS | ERTLPN % NOT ABS | LRTLPN % NOT ABS | SWBPGR % NOT ABS |
|---|---|---|---|---|---|---|---|
| Mean1 | 5.5 | 4.5 | 100.0 | 95.7 | 88.0 | 87.3 | 53.6 |
| Mean2 | 3.8 | 4.0 | 92.6 | 95.3 | 81.4 | 79.6 | 34.0 |
| Locs | 2 | 1 | 2 | 6 | 16 | 24 | 2 |
| Reps | 4 | 2 | 3 | 9 | 22 | 30 | 4 |
| Diff | 1.8 | 0.5 | 7.4 | 0.5 | 6.6 | 7.7 | 19.6 |
| Prob | 0.395 | | 0.043 | 0.918 | 0.014 | 0.131 | 0.343 |

All publications, patents and patent applications mentioned in the specification are indicative of the level of those skilled in the art to which this invention pertains. All such publications, patents and patent applications are incorporated by reference herein for the purpose cited to the same extent as if each was specifically and individually indicated to be incorporated by reference herein.

The foregoing invention has been described in detail by way of illustration and example for purposes of clarity and understanding. However, it is obvious that certain changes and modifications such as backcross conversions and mutations, somoclonal variants, variant individuals selected from large populations of the plants of the instant inbred and the like may be practiced within the scope of the invention, as limited only by the scope of the appended claims.

What is claimed is:

1. A seed comprising at least one set of the chromosomes of maize inbred line PH87P, representative seed of said line having been deposited under ATCC Accession No. PTA-4879.

2. A maize plant produced by growing the seed of claim 1.

3. A maize plant part of the maize plant of claim 2.

4. An F1 hybrid maize seed produced by crossing a plant of maize inbred line designated PH87P, representative seed of said line having been deposited under ATCC Accession No. PTA-4879, with a different maize plant and harvesting the resultant F1 hybrid maize seed, wherein said F1 hybrid maize seed comprises two sets of chromosomes and one set of the chromosomes is the same as maize inbred line PH87P.

5. A maize plant produced by growing the F1 hybrid maize seed of claim 4.

6. A maize plant part of the maize plant of claim 5.

7. An F1 hybrid maize seed comprising an inbred maize plant cell of inbred maize line PH87P, representative seed of said line having been deposited under ATCC Accession No. PTA-4879.

8. A maize plant produced by growing the F1 hybrid maize seed of claim 7.

9. The F1 hybrid maize seed of claim 7 wherein the inbred maize plant cell comprises two sets of chromosomes of maize inbred line PH87P.

10. A maize plant produced by growing the F1 hybrid maize seed of claim 9.

11. A process of introducing a desired trait into maize inbred line PH87P comprising:
    (a) crossing PH87P plants grown from PH87P seed, representative seed of which has been deposited under ATCC Accession Number PTA-4879, with plants of another maize line that comprise a desired trait to produce F1 progeny plants, wherein the desired trait is selected from the group consisting of waxy starch, male sterility, herbicide resistance, insect resistance, bacterial disease resistance, fungal disease resistance, and viral disease resistance;
    (b) selecting F1 progeny plants that have the desired trait to produce selected F1 progeny plants;
    (c) crossing the selected progeny plants with the PH87P plants to produce backcross progeny plants;
    (d) selecting for backcross progeny plants that have the desired trait and the alleles of inbred line PH87P at the SSR loci listed in Table 2 to produce selected backcross progeny plants; and (e) repeating steps (c) and (d) to produce backcross progeny plants that comprise the desired trait and comprise at least 95% of the alleles of inbred line PH87P at the SSR loci listed in Table 2.

12. A plant produced by the process of claim 11, wherein the plant comprises at least 95% of the alleles of inbred line PH87P at the SSR loci listed in Table 2.

13. A maize plant having all the physiological and morphological characteristics of inbred line PH87P, wherein a sample of the seed of inbred line PH87P was deposited under ATCC Accession Number PTA-4879.

14. A process of producing maize seed, comprising crossing a first parent maize plant with a second parent maize plant, wherein one or both of the first or the second parent maize plants is the plant of claim 13, wherein seed is allowed to form.

15. The maize seed produced by the process of claim 14.

16. The maize seed of claim 15, wherein the maize seed is hybrid seed.

17. A hybrid maize plant, or its parts, produced by growing said hybrid seed of claim 16.

18. The maize plant of claim 13, further comprising an SSR profile in accordance with the profile shown in Table 2.

19. A cell of the maize plant of claim 13.

20. The cell of claim 19, wherein said cell is further defined as having an SSR profile in accordance with the profile shown in Table 2.

21. A seed comprising the cell of claim 20.

22. The maize plant of claim 13, further defined as having a genome comprising a single gene conversion.

23. The maize plant of claim 22, wherein the single gene was stably inserted into the maize genome by transformation.

24. The maize plant of claim 22, wherein the gene is selected from the group consisting of a dominant allele and a recessive allele.

25. The maize plant of claim 22, wherein the gene confers a trait selected from the group consisting of herbicide tolerance; insect resistance; resistance to bacterial, fungal, nematode or viral disease; waxy starch; male sterility and restoration of male fertility.

26. The maize plant of claim 13, wherein said plant is further defined as comprising a gene conferring male sterility.

27. The maize plant of claim 13, wherein said plant is further defined as comprising a transgene conferring a trait selected from the group consisting of male sterility, herbicide resistance, insect resistance and disease resistance.

28. A method of producing a maize plant comprising the steps of:
 (a) growing a progeny plant produced by crossing the plant of claim 13 with a second maize plant;
 (b) crossing the progeny plant with itself or a different plant to produce a seed of a progeny plant of a subsequent generation;
 (c) growing a progeny plant of a subsequent generation from said seed and crossing the progeny plant of a subsequent generation with itself or a different plant; and
 (d) repeating steps (b) and (c) for an additional 0-5 generations to produce a maize plant.

29. The method of claim 28 wherein the produced maize plant is an inbred maize plant.

30. The method of claim 29, further comprising the step of crossing the inbred maize plant with a second, distinct inbred maize plant to produce an F1 hybrid maize plant.

31. A method for developing a second maize plant in a maize plant breeding program comprising applying plant breeding techniques to a first maize plant, or parts thereof, wherein said first maize plant is the maize plant of claim 13, and wherein application of said techniques results in development of said second maize plant.

32. The method for developing a maize plant in a maize plant breeding program of claim 31 wherein plant breeding techniques are selected from the group consisting of recurrent selection, backcrossing, pedigree breeding, restriction fragment length polymorphism enhanced selection, genetic marker enhanced selection, and transformation.

33. A method of plant breeding comprising the steps of:
 (a) obtaining a molecular marker profile of maize inbred line PH87P, representative seed of said line having been deposited under ATCC Accession No. PTA-4879;
 (b) obtaining an F1 hybrid seed for which the maize plant of claim 11 is a parent;
 (c) crossing a plant grown from the F1 hybrid seed with a different maize plant; and
 (d) selecting progeny that retain the molecular marker profile of PH87P.

* * * * *